United States Patent [19]
Stogniew et al.

[11] Patent Number: 6,017,922
[45] Date of Patent: Jan. 25, 2000

[54] THERMALLY STABLE TRIMETREXATES AND PROCESSES FOR PRODUCING THE SAME

[75] Inventors: Martin Stogniew, Blue Bell, Pa.; Ingomar Grafe, Nürnberg; Johann Mörsdorf, Langenzenn, both of Germany

[73] Assignee: U.S. Bioscience, Inc., Conshohocken, Pa.

[21] Appl. No.: 09/080,290

[22] Filed: May 18, 1998

[51] Int. Cl.$^7$ ........................ A61K 31/505; C07D 239/95
[52] U.S. Cl. ............................................ 514/260; 544/291
[58] Field of Search .............................. 544/291; 514/260

[56] References Cited

U.S. PATENT DOCUMENTS

| | | | |
|---|---|---|---|
| 3,560,502 | 2/1971 | Davoll | 544/291 |
| 4,376,858 | 3/1983 | Colbry | 544/291 |
| 4,391,809 | 7/1983 | Elslager | 424/251 |
| 4,677,219 | 6/1987 | Berman et al. | 558/419 |
| 5,424,471 | 6/1995 | Kennedy et al. | 558/146 |
| 5,591,731 | 1/1997 | Kennedy et al. | 514/114 |

FOREIGN PATENT DOCUMENTS

| | | |
|---|---|---|
| 0 051 415 | 5/1982 | European Pat. Off. |
| 0 253 396 | 1/1988 | European Pat. Off. |
| 1104576 | 2/1968 | United Kingdom. |
| 1345502 | 1/1974 | United Kingdom. |

OTHER PUBLICATIONS

Berge et al., *J. Pharmaceutical Sciences*, 66(1):1–19 (1977).
Hempel et al., *Cancer Biochem. Biophys.*, 10:25–30 (1988).
Hicks et al., *J. Labelled Compounds Radiopharm.*, 29(4):415–429 (1991).
McElvain, *The Characterization of Organic Compounds*, Revised Edition, The Macmillan Co., pp. 44–47,72–75 (1953).
*Physicians' Desk Reference*, 51st ed., pp. 2761–2764 (1997).
Schornagel et al., *Biochem. Pharmacology*, 33(20):3251–3255 (1984).
Stetson et al., *J. Chromatography*, 464:163–171 (1989).
Sutton et al., *J. Med. Chem.*, 30:1843–48 (1987).
Wong et al., *Drug Metabolism and Disposition*, 18(6):980–986 (1990).
Cell cycle effects of trimextrexate (CI–898), *Cancer Chemotherapy and Pharmacology*, Hook et al., vol. 16, No. 2, 1986, pp. 116–120.
Trimextrexate glucuronate, *Medicamentos de Actualidad (Drugs of Today)*, C. Robinson, vol. 30, No. 5, Jul. 1994.

*Primary Examiner*—Richard L. Raymond
*Attorney, Agent, or Firm*—Pennie & Edmonds, LLP

[57] ABSTRACT

The present invention provides for thermally stable forms of 2,4-diamino-5-methyl-6-[(3,4,5-trimethoxyanilino)methyl] quinazoline, or trimetrexate. A crystalline 2,4-diamino-5-methyl-6-[(3,4,5-trimethoxyanilino)methyl] quinazoline monohydrate, or trimextrexate monohydrate, belonging to the space group $P\bar{1}(\#2)$ and having a triclinic cell with dimensions of about a=7.699 Å, b=9.606 Å and c=13.012 Å is disclosed. A novel Schiff base compound, 2,4-diamino-5-methyl-6-[(3,4,5-trimethoxyphenylimino)-methinyl] quinazoline, is also disclosed. The present invention further provides novel methods of producing stable trimextrexate free base compounds, including crystalline trimextrexate monohydrate. The crystalline monohydrate form provides increased stability over the anhydrous form.

19 Claims, 8 Drawing Sheets

THERMALLY STABLE TRIMETREXATES AND PROCESSES FOR PRODUCING THE SAME

1. FIELD OF THE INVENTION

The present invention is directed to thermally stable forms of trimetrexate useful in pharmaceutical preparations. In particular, the invention is directed toward trimetrexate monohydrate, and to processes for its preparation, including a purified crystalline form. Trimetrexate monohydrate has unexpected improved thermal stability over the anhydrous form, and is thereof particularly useful as a bulk drug substance and/or for preparing trimetrexate salts.

2. BACKGROUND OF THE INVENTION

Trimetrexate, 2,4-diamino-5-methyl-6-[(3,4,5-trimethoxyanilino)methyl] quinazoline is a useful pharmaceutical compound known to have antineoplastic, antiparasitic and antibacterial activity. The trimetrexate free base has the structure:

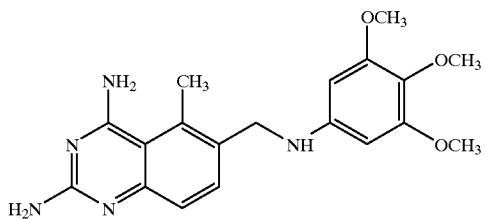

Trimetrexate is an inhibitor of the enzyme dihydrofolate reductase (DHFR) that is known to catalyze the synthesis of nucleotide precursors of DNA and RNA. Trimetrexate glucuronate is categorized as a folate antagonist, and has been clinically evaluated and is now approved for use in the treatment of *Pneumocystis carinii* pneumonia (PCP) in patients with acquired immune deficiency syndrome (AIDS) (*Physicians' Desk Reference*, 51st ed. (1997)). Inhibition of the DHFR enzyme results in cellular depletion of reduced folates, which are necessary for various cellular processes, including RNA and DNA synthesis, and ultimately results in cell death. It is this property that gives trimetrexate its antineoplastic, antiparasitic and antibacterial activity.

Trimetrexate has demonstrated antitumor activity against a range of experimental murine and human tumor cell lines, in vitro and in vivo. For example, trimetrexate has shown antitumor activity against murine cell lines such as L1210, L5178Y, S-180, W-256 in vitro. In addition, trimetrexate has shown antitumor activity against human tumor cells lines derived from breast, colon, lung, ovary, renal and melanoma cells in vitro. In vivo studies have demonstrated that trimetrexate has therapeutic utility against murine tumors such as B16 melanoma, colon 26 and 38, L1210 and p388 leukemia and CD8F mammary tumors. Other possible uses for trimetrexate include the treatment of malaria, psoriasis, rheumatoid arthritis and prophylaxis against *Pneumocystis carinii* pneumonia.

Trimetrexate as the free base is lipophilic, with very low water solubility (<0.1 mg/mL). Various trimetrexate salts with greater aqueous solubility are known. U.S. Pat. No. 4,376,858 to Colbry ("Colbry") discloses trimetrexate glucuronate as a preferred salt, due to its superior water solubility (>50 mg/mL), stability and the low toxicity of glucuronic acid. Colbry additionally discloses a method of preparing trimetrexate glucuronate wherein trimetrexate and glucuronic acid are dissolved in warm methanol and ethyl acetate and the solution is then cooled to precipitate the glucuronate salt. Additional trimetrexate salts and methods for making them are described in PCT publication WO96/21451.

Hicks et al., *J. Labelled Compounds Radiopharm.*, 29, 415 (1991), discloses another method of manufacture of trimetrexate glucuronate salt. In this method, trimetrexate and glucuronic acid are added to an aqueous solution in an ampoule, followed by lyophilization to form a solid, amorphous salt.

Trimetrexate is available as a commercial drug product under the commercial name Neutrexin® (U.S. Biosciences). The drug product was developed by Warner-Lambert/Parke-Davis as an injectable formulation presented as a 5 cc flint glass vial (USP Type I) containing 25 mg of trimetrexate and 15.35 mg D-glucuronic acid. The glucuronic acid is present in the formulation to help solubilize trimetrexate which is intrinsically insoluble in water. Neutrexin® provides trimetrexate glucuronate as a lyophilized powder, and is reconstituted prior to use in conjunction with leucovorin for the treatment of moderate to severe *Pneumocystis carinii* pneumonia in immunocompromised patients, e.g., those suffering from AIDS (U.S. Bioscience's Neutrexin for PCP, Scripp 1886/87, 31 (1994)).

The trimetrexate free base of the prior art, hereinafter referred to as "trimetrexate", is not stable for long-term storage, and rapidly degrades. To overcome the storage stability problem, trimetrexate is typically stored as a salt, due to the increased stability found for some trimetrexate salts. Stetson et al., *J. Chromatography*, 464, 163–171 (1989), discusses the stability of the trimetrexate glucuronate salt obtained from Warner Lambert/Parke-Davis, Pharmaceutical Research Division. This salt is apparently that obtained by the process disclosed in U.S. Pat. No. 4,376,858. Stetson indicates that the glucuronate salt has a half-life in solution of 51.6±0.8 days at 37° C.

The instability of trimetrexate creates numerous disadvantages. It is convenient to manufacture bulk trimetrexate and the final pharmaceutical formulation in different facilities to take advantage of specialization at different manufacturing plants, and economies of production, shipping, packaging, storage and the like. However, the instability of the prior art trimetrexate makes achieving these goals difficult. Additionally, degradation of trimetrexate between production and final formulation disadvantageously decreases the drug yield, and introduces additional costs in the manufacturing process necessary to produce a pharmaceutical-grade product.

Despite the disadvantages of trimetrexate, other, more stable non-salt forms of trimetrexate useful in pharmaceutical applications have not been identified. Indeed, USAN and the USP Dictionary of Drug Names show trimetrexate in only two forms: the anhydrous free base (trimetrexate), and the trimetrexate glucuronate salt.

Hempel et al., *Cancer Biochem. Biophys.*, 10, 25–30 (1988) ("Hempel"), discloses molecular structures of crystalline trimetrexate acetate monohydrate. Hempel additionally identifies a poorly-characterized, poly-hydrated trimetrexate free base. In Hempel, trimetrexate polyhydrate was crystallized from a methanol/water DMSO solution, and characterized by x-ray diffraction. The trimetrexate polyhydrate crystals belong to the C2/c space group and have structural parameters of a=36.051 Å, b=11.765 Å, c=10.623 Å and β=105.69°. The polyhydrate obtained by Hempel, however, is poorly characterized, having an unknown hydration number and consisting of poor quality crystals containing a number of disordered water molecules. In addition, Hempel does not disclose any stability advantages of the polyhydrated trimetrexate form.

Sutton et al., *J. Med. Chem.*, 30, 1843–48 (1987) ("Sutton"), reports the crystal structure of a DMSO-H$_2$O adduct of trimetrexate, trimetrexate dimethyl sulfoxide hydrate. Trimetrexate was crystallized as the DMSO hydrate, and the crystals analyzed by x-ray diffraction. The crystals of the trimetrexate-DMSO-H$_2$O adduct were found to be triclinic, belonging to the P-1 space group, and having structural parameters of a=9.423 Å, b=11.180 Å, c=12.399 Å and β=75.10°. However, the only form of trimetrexate produced and analyzed was the DMSO-H$_2$O adduct. In addition, Sutton does not disclose any thermal stability advantages of the DMSO-H$_2$O adduct. A stable, non-salt form of trimetrexate has not previously been produced and characterized.

It should be clear from the above that there is a need for a stable trimetrexate bulk drug substance that can be used to more efficiently and more cost-effectively produce a final trimetrexate pharmaceutical product. Further, there is a need for an efficient and rapid synthesis for this stable bulk drug substance.

3. SUMMARY OF THE INVENTION

The present invention relates to novel non-salt forms of trimetrexate, such as trimetrexate monohydrate (TMH), having improved thermal stability relative to the trimetrexate of the prior art. These stable, non-salt forms, which were previously unknown, unexpectedly provide enhanced stability over other forms of trimetrexate, in storage and for oral and intravenous administration of the drug. Additionally, trimetrexate monohydrate is non-hygroscopic, and possesses favorable manufacturing characteristics, including good flow properties. The invention also encompasses sterile forms of the monohydrate.

In its crystalline form, the preferred thermally stable trimetrexate, TMH, is characterized by a triclinic unit cell, with dimensions of a=7.699 Å, b=9.606 Å, and c=13.012 Å, and belongs to the space group P$\bar{1}$(#2). The identity and structure of TMH have been characterized by mass spectrometry, differential scanning calorimetry, thermal gravimetric analysis, and low-temperature x-ray crystallography.

The present invention also provides for novel chemical processes to produce trimetrexate monohydrate. In one preferred method, TMH is produced starting from the hydrated acetate salt. Briefly, the process comprises the steps of:

a. preparing a crude trimetrexate by treating trimetrexate acetate hydrate with ammonia;

b. recrystallizing the crude trimetrexate with dimethyl formamide (DMF) to produce a pure trimetrexate-DMF adduct;

c. converting the trimetrexate-DMF adduct to trimetrexate hydrochloride by forming a trimetrexate gluconate intermediate by reaction with gluconic acid and removal of gluconate with acetic acid; and d. forming pure, crystalline TMH by treating trimetrexate hydrochloride with ammonia.

This process allows the conversion of existing supplies of the trimetrexate acetate hydrate salt to the stable trimetrexate monohydrate of the present invention.

In another preferred method, TMH is produced by coupling quinazoline aldehyde with trimethoxyaniline via a Schiff base intermediate which, upon reduction with sodium borohydride, gives trimetrexate monohydrate. This process comprises the steps of:

a. producing a quinazoline aldehyde base by reacting quinazoline aldehyde formate or diformate with ammonia;

b. coupling the quinazoline aldehyde base with trimethoxyaniline to produce a quinazoline Schiff base;

c. reducing the quinazoline Schiff base to trimetrexate acetate hydrate by reaction with sodium borohydride; and d. preparing pure trimetrexate monohydrate from trimetrexate acetate hydrate via a 2-methoxypropanol adduct and purifying the TMH product.

The quinazoline Schiff base, 2,4-diamino-5-methyl-6-[(3,4,5-trimethoxyphenylimino)-methinyl]quinazoline, the trimetrexate-DMF adduct, and the trimetrexate 2-methoxypropanol adduct are also novel compounds. The thermally stable, non-salt trimetrexates, trimetrexate monohydrate and quinazoline Schiff base, and processes for their preparation or synthesis are described in more detail below.

4. BRIEF DESCRIPTION OF THE FIGURES

Figure 7:
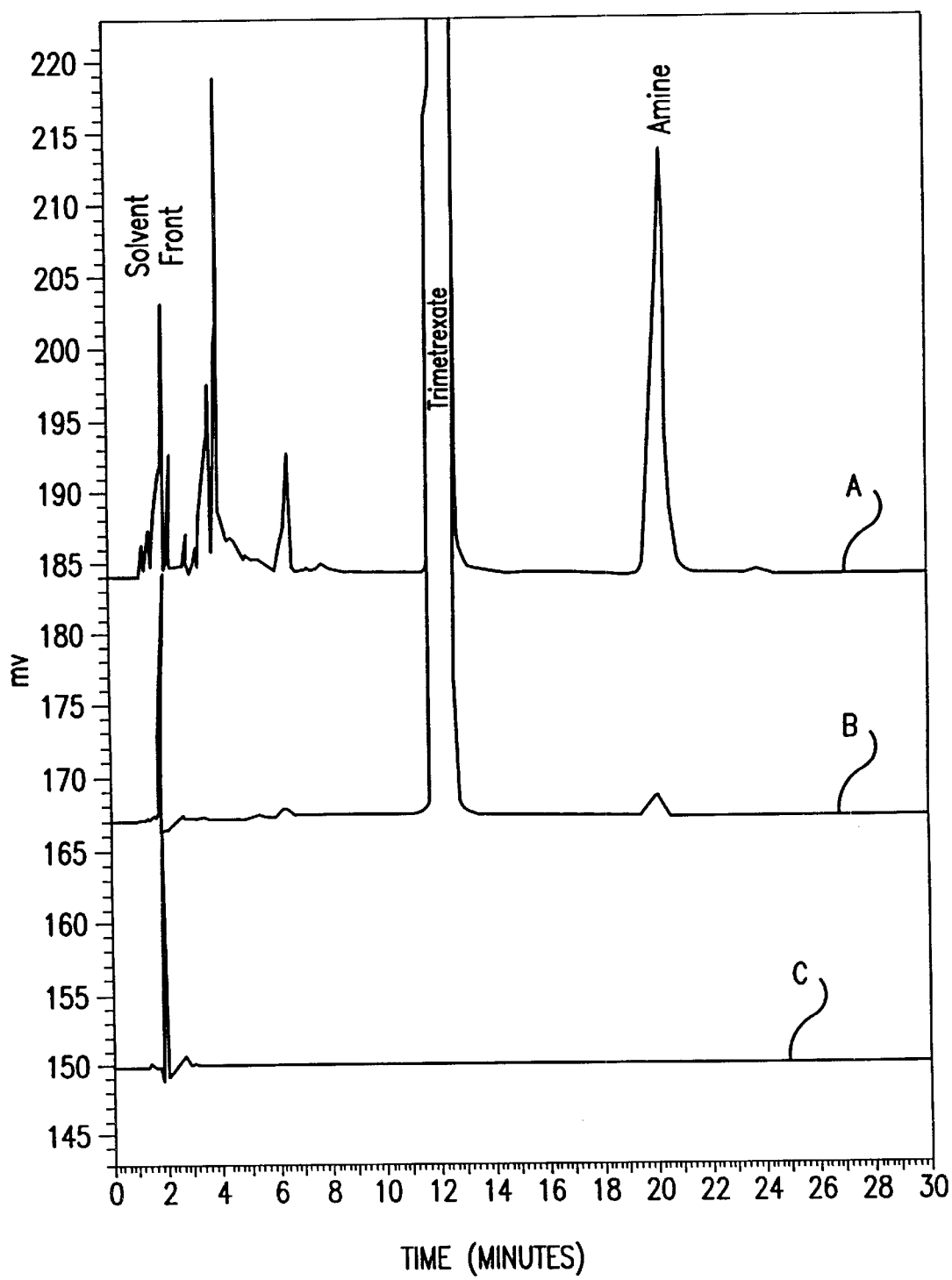

FIG. 7 is an HPLC chromatogram showing the relative stability of TMH over anhydrous trimetrexate. The peaks at about 2 to 7 minutes and the large peak at about 20 minutes in the anhydrous sample are indicative of sample degradation. The structure and UV absorption characteristics of the degradation product appearing at about 20 minutes, 6-aminomethyl-5-methyl-2,4-quinazolinediamine, are shown in Example 6.

5. DETAILED DESCRIPTION OF THE INVENTION

This invention is believed to represent the first disclosure of a thermally stable non-salt form of trimetrexate. Prior to this invention, trimetrexate was known to be thermally unstable, so that salt forms of trimetrexate, such as trimetrexate glucuronate and trimetrexate acetate, were used in manufacturing and production. However, described hereinafter are non-salt forms of trimetrexate which are believed to be thermally stable. Thus, the present invention encompasses thermally stable trimetrexate wherein the trimetrexate is a non-salt. Examples of thermally stable trimetrexates within the scope of the present invention are described below.

5.1. TRIMETREXATE MONOHYDRATE

Figure 1:
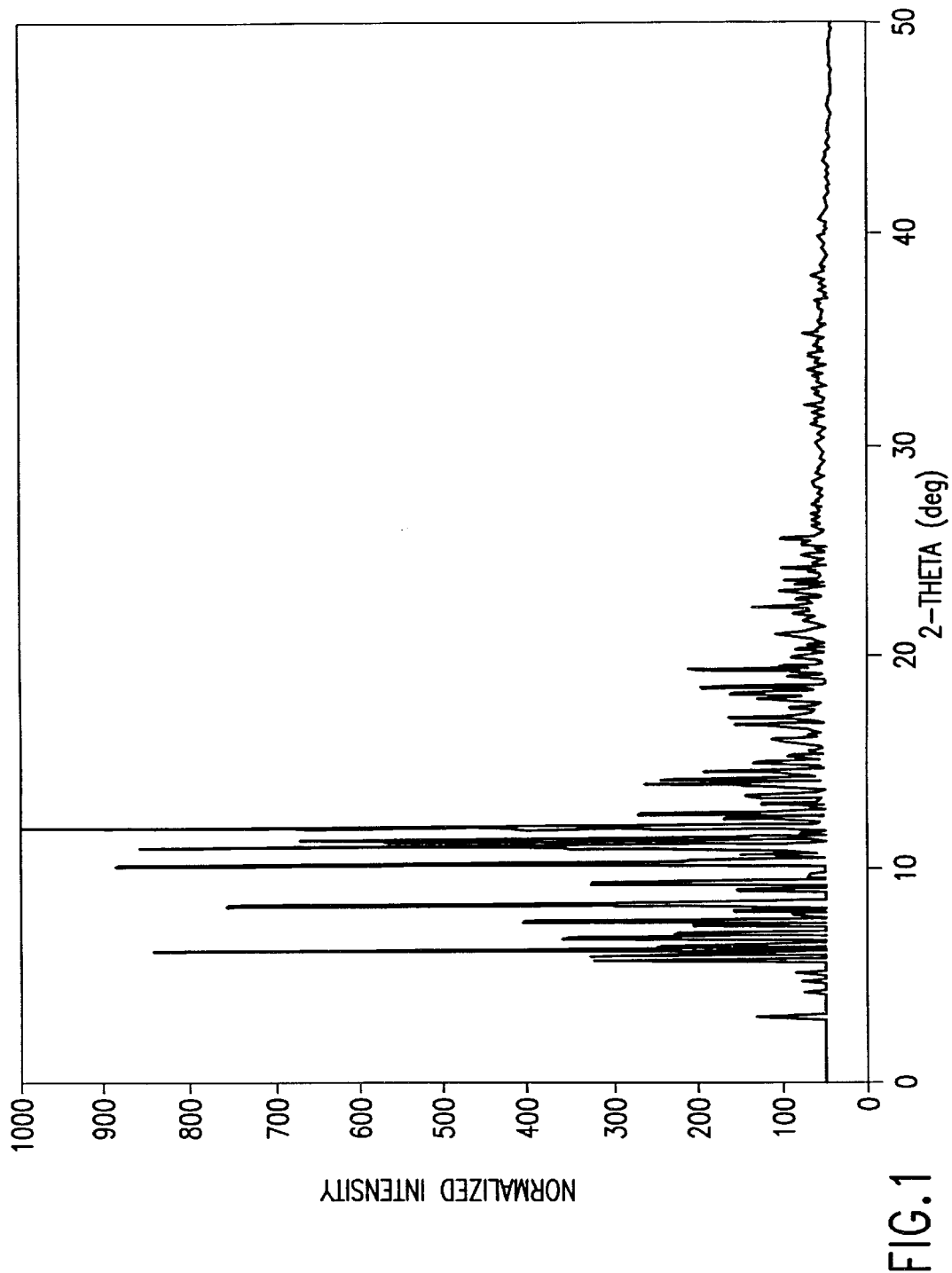
FIG. 1 is a graph of intensity versus diffraction angle for the x-ray diffraction of the crystalline trimetrexate monohydrate of the present invention.

In one embodiment, the present invention provides a trimetrexate monohydrate (TMH) free base which shows enhanced stability over trimetrexate. In its crystalline form, TMH is characterized by the x-ray diffraction pattern shown in FIG. 1. FIG. 1 shows the normalized relative intensity versus 2θ, for the x-ray diffraction of a single crystal of TMH at −175° C., using Mo-Kα radiation. The procedure to obtain this diffraction pattern is described in detail in Example 1, below.

Figure 2:
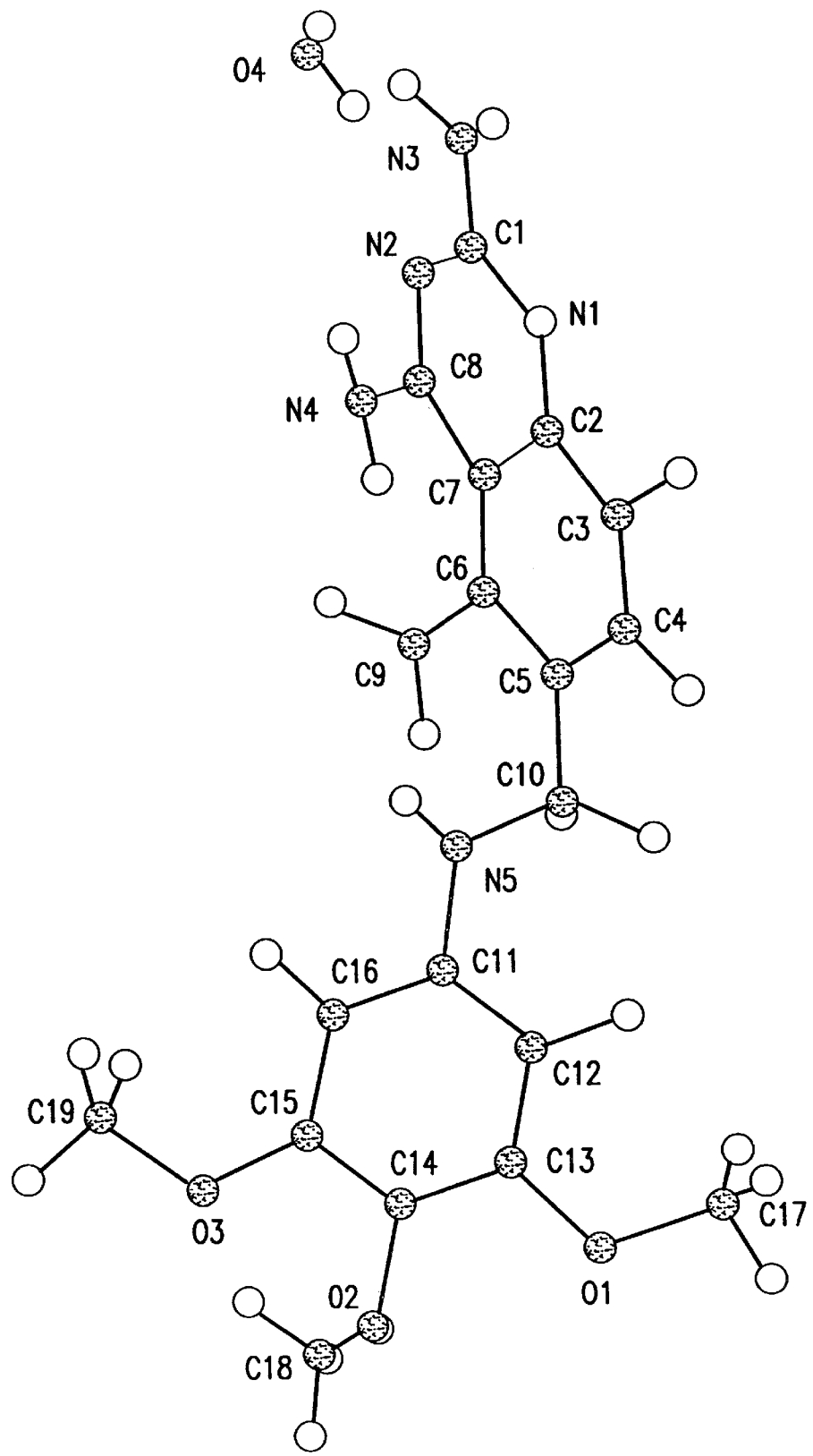
FIG. 2 shows the structure of crystalline TMH as obtained from the x-ray crystallography data.

FIG. 2 shows the molecular structure of the crystalline form of TMH. The atoms in FIG. 2 are numbered to correspond to the data presented in Tables 2–4 of Example 1. As the Figure shows, the trimetrexate molecule is associated with a water molecule at a well-defined position relative to the trimetrexate, near the amino group at position 2 (N3) of the heterocyclic ring. The atoms forming the quinazoline ring define a plane which has a dihedral angle of about 107.5° with respect to the plane containing the trimethoxyanilino group (see Table 5).

Crystalline trimetrexate monohydrate belongs to the space group P$\bar{1}$(#2) and crystallizes in a triclinic unit cell of dimensions:

| | | | |
|---|---|---|---|
| a = | 7.699(2) Å | α = | 77.702(8)° |
| b = | 9.606(3) Å | β = | 85.529(4)° |
| c = | 13.012(3) Å | γ = | 83.600(4)° |
| V = | 932.9(4) Å³ | | |

Figure 3A:
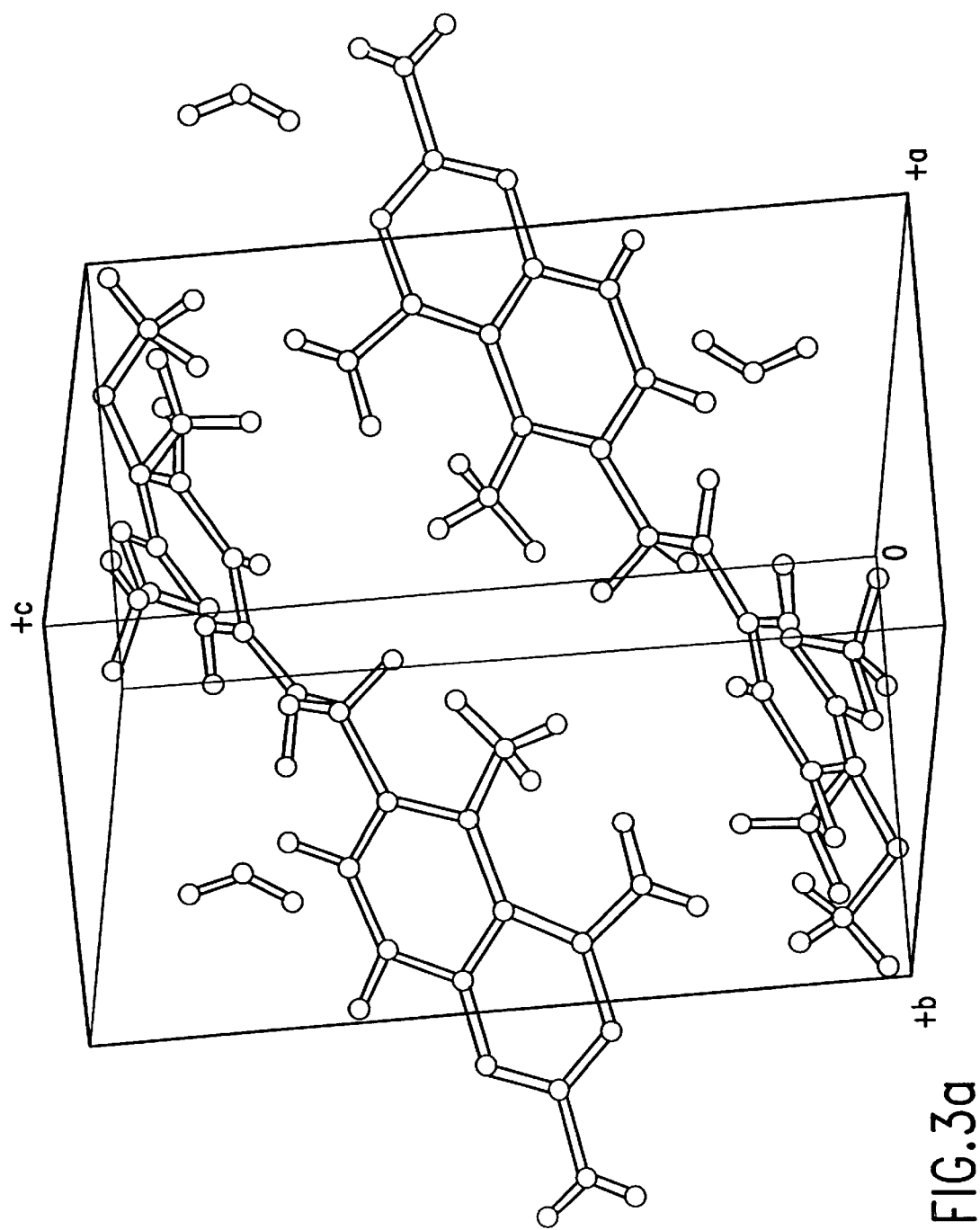
FIG. 3a shows the relative positions of trimetrexate molecules and their associated water molecules, within a crystalline TMH unit cell.
Figure 3B:
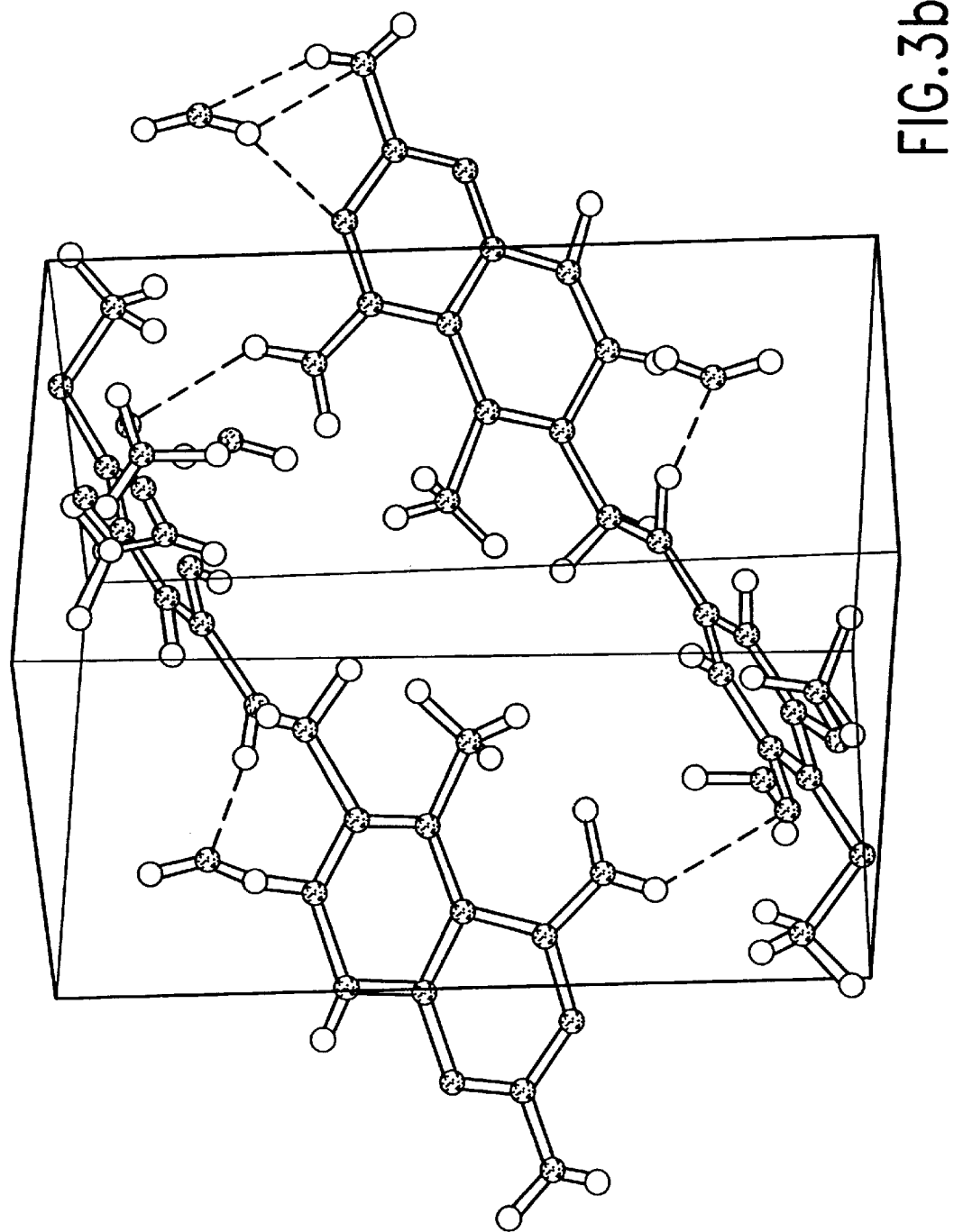
FIG. 3b shows the unit cell of FIG. 3a slightly rotated and shaded to emphasize atomic positions. The dotted lines show intramolecular hydrogen bonding interactions within a single trimetrexate molecule, intermolecular hydrogen bonding interactions between adjacent trimetrexate molecules, and hydrogen bonding interactions between trimetrexate and water, within a unit cell.

FIG. 3a shows the relative positions of two trimetrexate molecules and several associated water molecules, within a TMH unit cell. FIG. 3b shows the unit cell of FIG. 3a slightly rotated and shaded to show atomic positions. The dotted lines in FIG. 3b indicate hydrogen bonding interactions. As is clear from the Figure (see also Table 6), TMH is characterized by intermolecular hydrogen bonding interactions between adjacent trimetrexate molecules within the TMH crystal, intramolecular hydrogen bonding interactions within a single trimetrexate molecule, and hydrogen bonds between trimetrexate and the nearby associated water molecules. This high degree of hydrogen bonding likely contributes to the surprising and unexpected stability of TMH relative to the less stable trimetrexate.

The discovery of this thermally-stable trimetrexate is particularly important for the pharmaceutical industry, since this material can readily be used to prepare trimetrexate pharmaceutical salt(s) that are used to treat a variety of disorders, as described above.

5.2. METHOD OF PRODUCING TRIMETREXATE MONOHYDRATE FROM THE TRIMETREXATE ACETATE HYDRATE SALT

The present invention also encompasses methods of producing trimetrexate monohydrate. Trimetrexate previously synthesized by known methods was frequently converted to a salt such as acetate because of its instability. The present invention provides a method of producing the more stable monohydrate form of trimetrexate starting from the purified or crude acetate salt.

The trimetrexate acetate salt can be converted to pure trimetrexate monohydrate according to the process described below and referred to as Scheme 1. A detailed example of a synthesis according to Scheme 1 is given in the Examples below.

In a step of the TMH production, the crude trimetrexate acetate salt is converted into a crude trimetrexate by removal of the associated acetate molecule, as shown in Step 1:

Step 1.

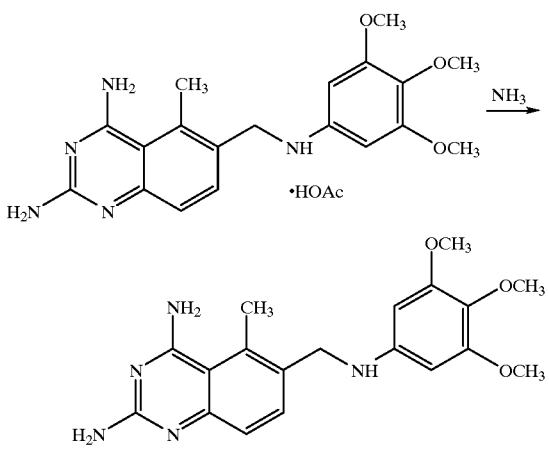

The starting material, crude trimetrexate acetate, need not be of particular purity in order to produce a highly pure, pharmaceutical-grade TMH product. In particular, the trimetrexate acetate can contain significant amounts of degradation products and still be suitable for use in the method of the present invention.

In Step 1, trimetrexate acetate is dissolved in a polar solvent or solvent mixture such as an aqueous alcoholic solvent, preferably a mixture of n-butanol and water, and most preferably a mixture of n-butanol and water in a ratio of from about 10:1 to about 1:2, with a ratio of about 4:1 being most preferred. A base, preferably aqueous ammonia, is added to react with the acetate resulting in the loss of ammonium acetate. Preferably, a small catalytic amount of sodium metabisulfite is also added. Auxiliary agents such as Tonsil (bentonite) and Supercel may also be added. The reaction is facilitated by heating the solution to a gentle reflux, preferably about 90° C., and stirring for about 10 minutes. The mixture is then filtered and washed, then heated to about 70° C. and ammonia is added. The crude trimetrexate base which crystallizes is then washed with a polar solvent such as water or alcohol, preferably a mixture of water and ethanol.

In another step, the crude trimetrexate base is converted into a pure dimethylformamide (DMF) adduct.

Step 2.

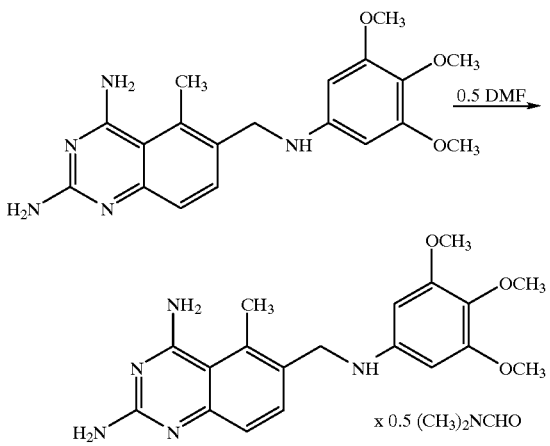

The crude trimetrexate base is dissolved in a mixture of DMF and water, preferably in a v/v ratio of about 10:1. The solution is initially heated to about 100° C., then a polar component such as an alcohol, preferably ethanol, is added as the solution cools to about 55–60° C. where crystallization occurs. The resulting crystals are then washed with ethanol to yield a pure trimetrexate DMF adduct. This trimetrexate-DMF adduct is itself a novel compound and is included within the scope of the invention.

In another step, the DMF adduct is converted to trimetrexate hydrochloride, via a trimetrexate gluconate intermediate.

Step 3.

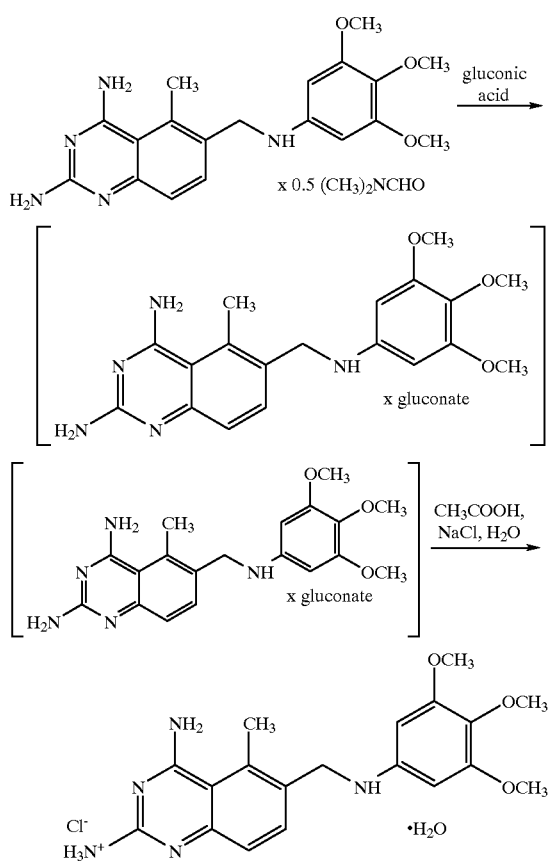

The gluconate is readily formed by suspending the DMF adduct in warm water, and adding a source of gluconate such as gluconic acid. Preferably, Supercel® and a small amount of activated charcoal are also added. The mixture is stirred at about 50° C. for about 10 minutes, and filtered. The hydrochloride salt can be formed by reacting the gluconate with a suitable acid, such as acetic acid, and stirring at about 50° C. for about 10 minutes with an aqueous sodium chloride solution. The resulting crystals can be filtered and washed with water or alcohol, preferably ethanol, or mixtures thereof to give the trimetrexate hydrochloride salt.

Finally, in a last step, the trimetrexate hydrochloride salt is converted into the pure trimetrexate monohydrate.

Step 4.

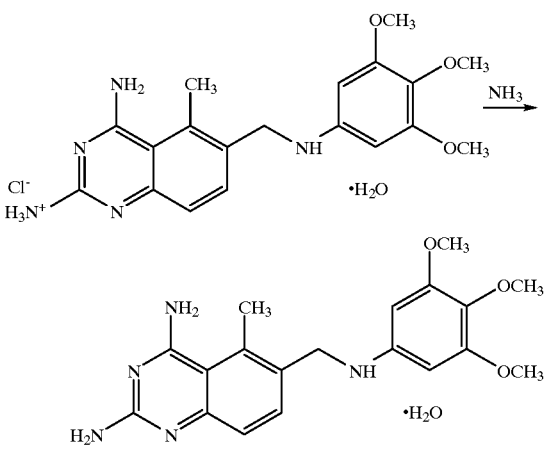

The reaction is run in a polar solvent or solvent mixture, at about 80° C. Suitable solvents include various alcohols that are well known to the skilled artisan to be miscible with water. Preferably the solvent is a mixture of water and n-butanol, with the majority of the solvent being water; a preferred ratio is about 3:1. Addition of a base precipitates the trimetrexate monohydrate. The base can be a water-soluble organic amine, such as trimethylamine or ethanolamine, or preferably ammonia. The precipitated trimetrexate monohydrate can be filtered, washed (ethanol/water) and dried under vacuum, and optionally sterilized.

The TMH thus obtained can be optionally sieved and blended, as desired.

5.3. METHOD OF PRODUCING TRIMETREXATE MONOHYDRATE FROM THE QUINAZOLINE ALDEHYDE FORMATE OR DIFORMATE

The present invention also encompasses a method of producing TMH starting from quinazoline aldehyde formate or diformate, according to the process described below and referred to as Scheme 2. A detailed example of a synthesis according to Scheme 2 is given in the Examples below.

In a step of the process, quinazoline aldehyde formate or diformate is converted to 2,4-diamino-5-methyl-6-quinazoline carboxaldehyde hydrate (quinazoline aldehyde base).

Step 1

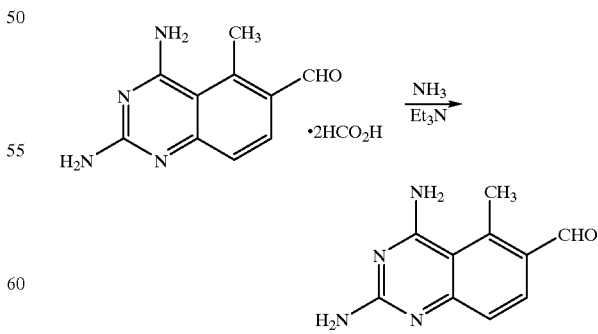

The starting material, quinazoline aldehyde formate or diformate, can be synthesized by reduction of the corresponding nitrile, 2,4-diamino-5-methyl-6-quinazoline carbonitrile, with Raney nickel and formic acid (see *Bio-* chem. Pharmacology, 33, 3251 (1984), which is hereby incorporated by reference). Quinazoline aldehyde formate or diformate is dissolved in a polar solvent or solvent mixture such as an aqueous alcoholic solvent, preferably a mixture of n-butanol and water in a ratio of about 1.5:1. The free aldehyde base is obtained by stirring the solution at a gentle reflux temperature of about 90° C. for about 20 minutes, in the presence of triethylamine, ammonia and a small amount of ethylenediaminetetraacetic acid (EDTA). The resulting crystals are filtered and washed with alcohol and water, preferably n-butanol. The crystals may optionally be washed repeatedly with different alcohols, or water or mixtures thereof. Preferably, n-butanol, ethanol and then water are used.

In another step, quinazoline aldehyde is coupled to trimethoxyaniline to produce 2,4-diamino-5-methyl-6-[(3,4,5-trimethoxyphenylimino)-methinyl]quinazoline (quinazoline Schiff base).

Step 2

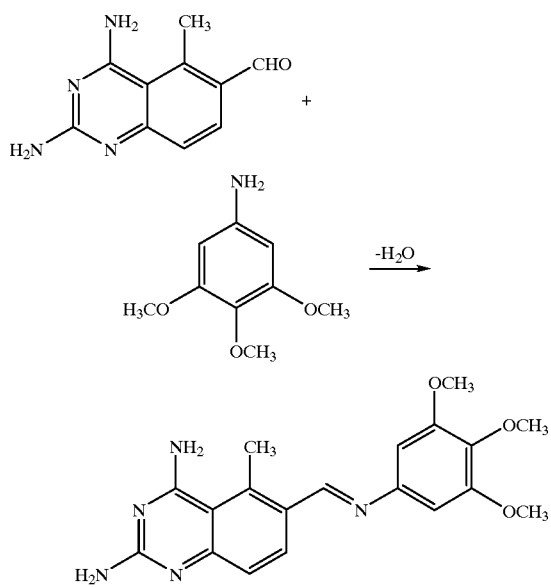

The solvent is preferably a mixture of an aliphatic alcohol which forms an azeotrope with water, and a hydrocarbon. Suitable alcohols include, but are not limited to, n-butanol, and suitable hydrocarbons include, but are not limited to, toluene, xylene or chlorobenzene. Preferably, the solvent is a mixture of n-butanol and toluene in a ratio of about 5:1. The reaction is conveniently carried out by heating the wet quinazoline aldehyde base in the alcohol/toluene solvent to an azeotropic point, and distilling the water of dehydration. When n-butanol and toluene are used in a ratio of 5:1, the distillation temperature varies from about 89° C. initially up to about 110° C. (liquid phase temperature). The resulting Schiff base can be filtered off, and washed with alcohol, preferably n-butanol, and an ether, preferably t-butyl methyl ether.

In another step, the quinazoline Schiff base is reduced to trimetrexate, and precipitated as the acetate salt.

Step 3

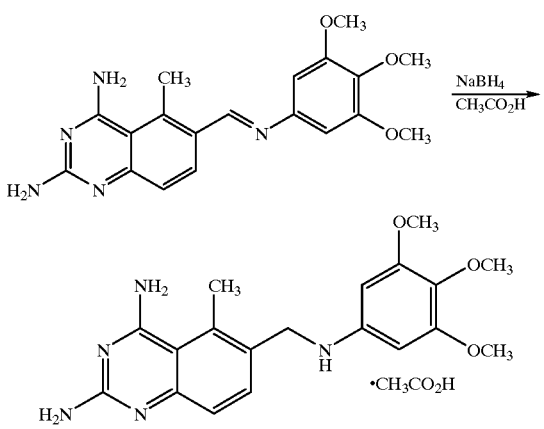

The Schiff base is readily hydrolyzed, so the reduction should take place immediately following Step 2. The solvent used is preferably a mixture of tetrahydrofuran (THF) and water in a ratio of about 4:1. However, other ethers known to the skilled artisan, such as 1,4-dioxane, can also be used. Sodium carbonate, trimethoxyaniline and the quinazoline Schiff base are heated to about 45° C., and an aqueous sodium borohydride solution is slowly added over several hours, while the reaction is kept under nitrogen protection. After the reduction is complete, most of the THF (about 90%) can be distilled off, and an alcohol-water mixture is added. Various alcohols known to the skilled artisan may be used, but the alcohol selected should not be completely miscible with water. Suitable alcohols include isobutanol and n-butanol. Preferably, a mixture of n-butanol and water in a 2:1 ratio is used. The mixture can be filtered and washed with water to yield a crude trimetrexate base. The acetate salt is formed by suspending the crude base in a polar solvent such as an ethanol/water mixture, heating to about 70° C., adding lactic acid and acetic acid, and mixing the solution with tonsil and a small amount of activated charcoal. The filtrate is mixed with sodium acetate and acetic acid for about 30 minutes at 70–75° C., then cooled to 20° C., filtered and washed with acetic acid.

Finally, the pure TMH product is formed from the acetate salt.

Step 4

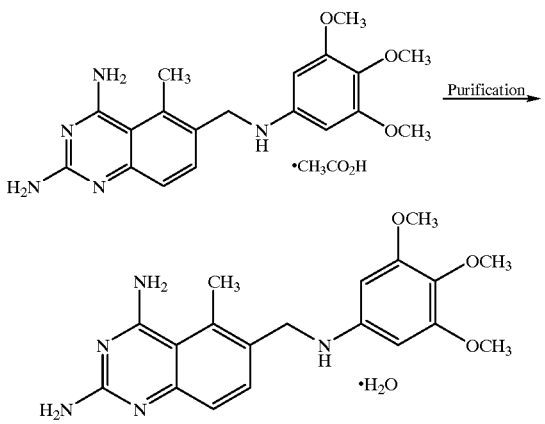

The trimetrexate acetate is first converted to a 2-methoxypropanol adduct, then recrystallized as the free base. The trimetrexate 2-methoxypropanol adduct is itself a novel compound included within the scope of the invention. The trimetrexate monohydrate product is dried under vacuum (40–80° C., preferably about 50° C., for 2–40 hours, preferably about 4–8 hours), and optionally sieved, blended and sterilized.

5.4. QUINAZOLINE SCHIFF BASE

The present invention also encompasses the novel chemical compound having the formula

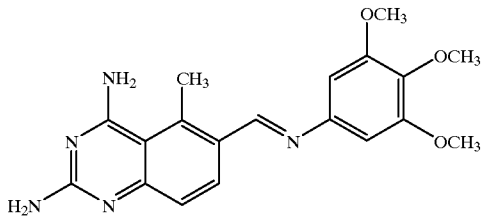

This compound, 2,4-diamino-5-methyl-6-[(3,4,5-trimethoxyphenylimino)-methinyl]quinazoline (quinazoline Schiff base) is produced by the method shown above in Scheme 2. The quinazoline Schiff base is a yellow powder with a molecular formula $C_{19}H_{21}N_5O_3$ and a formula weight of 367.41 g/mol. The characterization of this compound is described in the Examples below.

Certain embodiments of the invention are illustrated, and not limited, by the following working examples.

6. EXAMPLES

6.1. EXAMPLE 1: X-ray Crystallography of TMH

The molecular and crystal structure of crystalline trimetrexate monohydrate was determined by x-ray diffraction. Crystal survey, unit cell determination, and data collection were performed using Mo-Kα radiation at −175° C. Preliminary analysis of the unit cell constants indicated a triclinic unit cell. Intensity statistics obtained during data collection indicated the presence of a centrosymmetric space group, suggesting the space group P-1. The structure was solved by direct methods.

All non-hydrogen atoms were initially refined using isotropic and then anisotropic temperature factors. Redundant data were averaged, yielding an $R_{av}$ of 0.065. Hydrogen atoms were located by examination of an electron density difference map but were not refined. After hydrogen atoms were added, three additional cycles of full-matrix refinement were performed.

Data Collection

A clear needle crystal of $C_{19}H_{23}O_3N_5 \cdot H_2O$ having approximate dimensions of 0.13×0.15×0.40 mm was mounted on a glass fiber. All measurements were made on a Quantum CCD area detector coupled with a Rigaku AFC7 diffractometer with graphite monochromated Mo-Kα radiation.

Cell constants and an orientation matrix for data collection corresponded to a primitive triclinic cell with dimensions:

| | | | |
|---|---|---|---|
| a = | 7.699(2) Å | α = | 77.702(8)° |
| b = | 9.606(3) Å | β = | 85.529(4)° |

-continued

| | | | |
|---|---|---|---|
| c = | 13.012(3) Å | γ = | 83.600(4)° |
| V = | 932.9(4) Å³ | | |

For Z=2 and a formula weight of 387.44, the calculated density is 1.38 g/cm³. Based on a statistical analysis of intensity distribution, and the successful refinement of the structure, the space group was determined to be P$\bar{1}$(#2).

The data were collected at a temperature of −175±1° C. to a maximum 2θ value of 58.5°. Data were collected in 0.50° oscillations with 98.0 second exposures. A sweep of data was done using φ oscillations from 0.0 to 190.0° at Χ=0° and a second sweep was performed using ω oscillations between −17.0 and 23.0° at Χ=90.0°. The crystal-to-detector distance was 38.60 mm. The detector swing angle was −5.00°.

Data Reduction

Of the 7355 reflections which were collected, 3379 were unique ($R_{int}$, =0.065); equivalent reflections were merged. The linear absorption coefficient, μ, for Mo-Kα radiation is 1.0 cm⁻¹. The data were corrected for Lorentz and polarization effects. A correction for secondary extinction was applied (coefficient=1.54877×10⁻⁶).

Structure Solution and Refinement

The structure was solved by direct methods (SAPI91: Fan Hai-Fu (1991): Structure Analysis Programs with Intelligent Control, Rigaku Corporation, Tokyo, Japan). The non-hydrogen atoms were refined anisotropically. Hydrogen atoms were included but not refined. The final cycle of full-matrix least-squares refinement was based on 1537 observed reflections (I >3.00σ(I)) and 254 variable parameters and converged (largest parameter shift was 0.02 times its e.s.d.) with unweighted agreement factors of:

$R=\Sigma||F_o|-|F_c||/\Sigma|F_o|=0.049$ $R_w=[\Sigma w(|F_o|-|F_c|)^2/\Sigma F_o^2]^{1/2}$ The standard deviation of an observation of unit weight, defined by the function $[\Sigma w(|F_o|-|F_c|)^2/(N_o-N_v)]^{1/2}$ were $N_0$ and $N_v$ are the number of observations and the number of variables, respectively, was 2.41. The weighting scheme was based on counting statistics and included a factor (p=0.040) to downweight the intense reflections. Plots of $\Sigma w(|F_o|-|F_c|)^2$ versus $|F_o|$, reflection order in data collection, sinθ/λ and various classes of indices showed no unusual trends. The maximum and minimum peaks on the final difference Fourier map corresponded to 0.31 and −0.37 e⁻/Å³, respectively.

Neutral atom scattering factors were taken from Cromer and Weber (International Tables for X-ray Crystallography, Vol. IV, The Kynoch Press, Birmingham, England, Table 2.2A (1974)). Anomalous dispersion effects were included in $F_{calc}$ (Ibers, J. A. & Hamilton, W. C.; Acta Crystallogr., 17, 781 (1964)); the values for Δf' and Δf" were those of Creagh and McAuley (International Tables for Crystallography, Vol. C, (A. J. C. Wilson, ed.), Kluwer Academic Publishers, Boston, Table 4.2.6.8, pages 219–222 (1992)). The values for the mass attenuation coefficients are those of Creagh and Hubbell (International Tables for Crystallography, Vol. C, (A. J. C. Wilson, ed.), Kluwer Academic Publishers, Boston, Table 4.2.4.3, pages 200–206 (1992)). All calculations were performed using the teXsan crystallographic software package (teXsan for Windows: Crystal Structure Analysis Package, Molecular Structure Corporation (1997)).

The experimental details are summarized in Table 1. The atomic positions, bond lengths, bond angles, least squares planes, and hydrogen bonding distances and angles are presented in Tables 2–6.

TABLE 1

X-Ray Diffraction Analysis of TMH

A. Crystal Data

| | |
|---|---|
| Empirical Formula | $C_{19}H_{25}O_4N_5$ |
| Formula Weight | 387.44 |
| Crystal Color, Habit | clear, needle |
| Crystal Dimensions | 0.13 × 0.15 × 0.40 mm |
| Crystal System | Triclinic |
| Lattice Type | Primitive |
| Lattice Parameters: | a = 7.699(2) Å |
| | b = 9.606(3) Å |
| | c = 13.012(3) Å |
| | α = 77.702(8)° |
| | β = 85.529(4)° |
| | γ = 83.600(4)° |
| | V = 932.9(4) Å$^3$ |
| Space Group | P$\bar{1}$(#2) |
| Z value | 2 |
| $D_{calc}$ | 1.379 g/cm$^3$ |
| $F_{000}$ | 412.00 |
| $\mu$ (MoKα) | 0.99 cm$^{-1}$ |

B. Intensity Measurements

| | |
|---|---|
| Diffractometer | Quantum CCD/Rigaku AFC7 |
| Radiation | MoKα (λ = 0.71069 Å) graphite monochromated |
| Detector Aperture | 81.466 mm × 81.466 mm |
| Data Images | 460 exposures @ 98.0 sec |
| φ Oscillation Range (χ = 0) | 0.0–190.0° |
| ω Oscillation Range (χ = 90.0) | −17.0–23.0° |
| Detector Position | 38.60 mm |
| Detector Swing Angle | −5.00° |
| 2θ$_{max}$ | 58.5° |
| No. Reflections Measured | Total: 7355 Unique: 3379 ($R_{int}$ = 0.065) |
| Corrections | Lorentz-polarization Secondary Extinction (coef: 1.54877e − 06) |

C. Structure Solution and Refinement

| | |
|---|---|
| Structure Solution | Direct Methods (SAPI91) |
| Refinement | Full-matrix least-squares |
| Function Minimized | $\Sigma w(|F_o| - |F_c|)^2$ |
| Least Squares Weights | $w = \dfrac{1}{\sigma^2(F_o)} = \left[\sigma_0^2(F_o) + \dfrac{p^2}{4}F_o^2\right]^{-1}$ |
| p-factor | 0.0400 |
| Anomalous Dispersion | All non-hydrogen atoms |
| No. Observations (I > 3.00σ(I)) | 1537 |
| No. Variables | 254 |
| Reflection/Parameter Ratio | 6.05 |
| Residuals: R; $R_w$ | 0.049; 0.033 |
| Goodness of Fit Indicator | 2.41 |
| Max Shift/Error Final Cycle | 0.02 |
| Max Peak in Final Diff. Map | 0.31 e$^-$/Å$^3$ |
| Min Peak in Final Diff. Map | −0.37 e$^-$/Å$^3$ |

TABLE 2

Atomic Coordinates and $B_{iso}/B_{eq}$ in TMH

| atom | x | y | z | $B_{eq}$ |
|---|---|---|---|---|
| O(1) | 0.3653(3) | 0.9624(3) | 0.1127(2) | 1.17(8) |
| O(2) | 0.1577(3) | 0.8262(3) | 0.0178(2) | 1.20(8) |
| O(3) | 0.2013(3) | 0.5439(3) | 0.0392(2) | 1.34(9) |
| O(4) | 1.1580(4) | −0.2362(3) | 0.8075(2) | 1.81(9) |
| N(1) | 1.2983(4) | 0.1235(4) | 0.5061(3) | 0.89(10) |
| N(2) | 1.0957(4) | 0.0206(4) | 0.6443(3) | 1.03(10) |
| N(3) | 1.3742(4) | −0.0874(4) | 0.6222(3) | 1.33(10) |
| N(4) | 0.8211(4) | 0.1176(4) | 0.6715(3) | 1.71(10) |
| N(5) | 0.6829(4) | 0.5050(4) | 0.2626(3) | 1.23(10) |
| C(1) | 1.2527(5) | 0.0245(5) | 0.5870(4) | 1.08(13) |
| C(2) | 1.1687(5) | 0.2310(5) | 0.4704(4) | 0.92(12) |
| C(3) | 1.2149(5) | 0.3367(5) | 0.3840(3) | 1.13(12) |
| C(4) | 1.0900(5) | 0.4438(5) | 0.3421(3) | 0.94(12) |
| C(5) | 0.9155(5) | 0.4463(5) | 0.3852(4) | 0.79(12) |
| C(6) | 0.8662(5) | 0.3457(5) | 0.4705(3) | 0.78(12) |
| C(7) | 0.9962(5) | 0.2337(5) | 0.5175(3) | 0.69(12) |
| C(8) | 0.9714(5) | 0.1243(5) | 0.6105(4) | 0.98(12) |
| C(9) | 0.6752(5) | 0.3496(5) | 0.5119(3) | 1.25(12) |
| C(10) | 0.7883(5) | 0.5662(5) | 0.3280(4) | 1.14(12) |
| C(11) | 0.5557(5) | 0.5905(5) | 0.1999(3) | 1.00(12) |
| C(12) | 0.5334(5) | 0.7388(5) | 0.1905(3) | 0.93(12) |
| C(13) | 0.4006(5) | 0.8162(5) | 0.1280(3) | 0.72(12) |
| C(14) | 0.2912(5) | 0.7471(5) | 0.0790(3) | 0.77(12) |
| C(15) | 0.3185(5) | 0.6005(5) | 0.0892(3) | 0.92(13) |
| C(16) | 0.4511(5) | 0.5186(5) | 0.1488(3) | 0.90(12) |
| C(17) | 0.4975(5) | 1.0382(5) | 0.1445(4) | 1.43(12) |
| C(18) | −0.0087(5) | 0.8361(5) | 0.0785(4) | 1.54(13) |
| C(19) | 0.2096(5) | 0.3909(5) | 0.0545(4) | 1.34(13) |
| H(1) | 1.3375 | −0.1703 | 0.6761 | 1.9640 |
| H(2) | 1.4773 | −0.0888 | 0.5781 | 1.9640 |
| H(3) | 1.3531 | 0.3345 | 0.3602 | 1.9640 |
| H(4) | 1.1199 | 0.5349 | 0.2755 | 1.9640 |
| H(5) | 0.6080 | 0.4232 | 0.4522 | 1.9640 |
| H(6) | 0.6514 | 0.3589 | 0.5731 | 1.9640 |
| H(7) | 0.6367 | 0.2424 | 0.5355 | 1.9640 |
| H(8) | 0.7338 | 0.1995 | 0.6536 | 1.9640 |
| H(9) | 0.8203 | 0.0598 | 0.7348 | 1.9640 |
| H(10) | 0.6884 | 0.5991 | 0.3816 | 1.9640 |
| H(11) | 0.8411 | 0.6672 | 0.2910 | 1.9640 |
| H(12) | 0.7357 | 0.3999 | 0.2501 | 1.9640 |
| H(13) | 0.6189 | 0.7960 | 0.2269 | 1.9640 |
| H(14) | 0.4926 | 1.0191 | 0.2280 | 1.9640 |
| H(15) | 0.6317 | 1.0242 | 0.1025 | 1.9640 |
| H(16) | 0.4502 | 1.1480 | 0.1195 | 1.9640 |
| H(17) | −0.0003 | 0.9006 | 0.1312 | 1.9640 |
| H(18) | −0.0391 | 0.7260 | 0.1209 | 1.9640 |
| H(19) | −0.0917 | 0.8909 | 0.0234 | 1.9640 |
| H(20) | 0.0927 | 0.3764 | 0.0101 | 1.9640 |
| H(21) | 0.3437 | 0.3439 | 0.0222 | 1.9640 |
| H(22) | 0.2070 | 0.3387 | 0.1297 | 1.9640 |
| H(23) | 0.4873 | 0.40006 | 0.1493 | 1.9640 |
| H(24) | 1.1678 | −0.1587 | 0.7529 | 1.9640 |
| H(25) | 1.1230 | −0.2322 | 0.8724 | 1.9640 |

$B_{eq} = (8/3)\pi^2(U_{11}(aa^*)^2 + U_{22}(bb^*)^2 + U_{33}(cc^*)^2 + 2U_{12}aa^*bb^*\cos\gamma + 2U_{13}aa^*cc^*\cos\beta + 2U_{23}bb^*cc^*\cos\alpha)$

TABLE 3

Bond Lengths (Å) in TMH

| atom | atom | distance | atom | atom | distance |
|---|---|---|---|---|---|
| O(1) | C(13) | 1.375(5) | O(1) | C(17) | 1.449(5) |
| O(2) | C(14) | 1.402(4) | O(2) | C(18) | 1.457(5) |
| O(3) | C(15) | 1.372(5) | O(3) | C(19) | 1.436(5) |
| O(4) | H(24) | 0.92 | O(4) | H(25) | 0.87 |
| N(1) | C(1) | 1.315(5) | N(1) | C(2) | 1.385(5) |
| N(2) | C(1) | 1.370(5) | N(2) | C(8) | 1.330(5) |
| N(3) | C(1) | 1.368(5) | N(3) | H(1) | 0.99 |
| N(3) | H(2) | 0.94 | N(4) | C(8) | 1.351(5) |
| N(4) | H(8) | 0.98 | N(4) | H(9) | 0.89 |
| N(5) | C(10) | 1.467(5) | N(5) | C(11) | 1.400(5) |
| N(5) | H(12) | 1.09 | C(2) | C(3) | 1.398(6) |
| C(2) | C(7) | 1.418(5) | C(3) | C(4) | 1.380(6) |
| C(3) | H(3) | 1.08 | C(4) | C(5) | 1.415(6) |
| C(4) | H(4) | 1.12 | C(5) | C(6) | 1.367(6) |
| C(5) | C(10) | 1.529(5) | C(6) | C(7) | 1.452(5) |
| C(6) | C(9) | 1.526(5) | C(7) | C(8) | 1.440(6) |
| C(9) | H(5) | 1.06 | C(9) | H(6) | 0.93 |

TABLE 3-continued

Bond Lengths (Å) in TMH

| atom | atom | distance | atom | atom | distance |
|---|---|---|---|---|---|
| C(9) | H(7) | 1.08 | C(10) | H(10) | 1.07 |
| C(10) | H(11) | 1.09 | C(11) | C(12) | 1.395(6) |
| C(11) | C(16) | 1.404(6) | C(12) | C(13) | 1.400(5) |
| C(12) | H(13) | 1.10 | C(13) | C(14) | 1.395(6) |
| C(14) | C(15) | 1.380(6) | C(15) | C(16) | 1.395(5) |
| C(16) | H(23) | 1.14 | C(17) | H(14) | 1.06 |
| C(17) | H(15) | 1.14 | C(17) | H(16) | 1.07 |
| C(18) | H(17) | 1.03 | C(18) | H(18) | 1.12 |
| C(18) | H(19) | 1.02 | C(19) | H(20) | 1.14 |
| C(19) | H(21) | 1.16 | C(19) | H(22) | 1.00 |

TABLE 4

Bond Angles (°) in TMH

| atom | atom | atom | angle | atom | atom | atom | angle |
|---|---|---|---|---|---|---|---|
| C13 | O1 | C17 | 115.9(3) | C14 | O2 | C18 | 112.1(3) |
| C15 | O3 | C19 | 117.8(3) | H24 | O4 | H25 | 125.6 |
| C1 | N1 | C2 | 116.0(4) | C1 | N2 | C8 | 116.4(4) |
| C1 | N3 | H1 | 119.4 | C1 | N3 | H2 | 113.5 |
| H1 | N3 | H2 | 124.8 | C8 | N4 | H8 | 115.1 |
| C8 | N4 | H9 | 119.4 | H8 | N4 | H9 | 122.1 |
| C10 | N5 | C11 | 121.2(4) | C10 | N5 | H12 | 114.2 |
| C11 | N5 | H12 | 122.4 | N1 | C1 | N2 | 127.5(4) |
| N1 | C1 | N3 | 118.2(4) | N2 | C1 | N3 | 114.3(4) |
| N1 | C2 | C3 | 116.6(4) | N1 | C2 | C7 | 122.2(4) |
| C3 | C2 | C7 | 121.2(4) | C2 | C3 | C4 | 119.5(4) |
| C2 | C3 | H3 | 116.0 | C4 | C3 | H3 | 124.2 |
| C3 | C4 | C5 | 120.6(5) | C3 | C4 | H4 | 123.1 |
| C5 | C4 | H4 | 116.3 | C4 | C5 | C6 | 121.4(4) |
| C4 | C5 | C10 | 115.2(4) | C6 | C5 | C10 | 123.4(4) |
| C5 | C6 | C7 | 119.1(4) | C5 | C6 | C9 | 119.7(4) |
| C7 | C6 | C9 | 121.2(4) | C2 | C7 | C6 | 118.2(4) |
| C2 | C7 | C8 | 114.9(4) | C6 | C7 | C8 | 126.9(4) |
| N2 | C8 | N4 | 113.8(4) | N2 | C8 | C7 | 122.7(4) |
| N4 | C8 | C7 | 123.5(4) | C6 | C9 | H5 | 104.0 |
| C6 | C9 | H6 | 115.1 | C6 | C9 | H7 | 110.1 |
| H5 | C9 | H6 | 106.0 | H5 | C9 | H7 | 119.0 |
| H6 | C9 | H7 | 103.1 | N5 | C10 | C5 | 108.4(4) |
| N5 | C10 | H10 | 100.0 | N5 | C10 | H11 | 116.6 |
| C5 | C10 | H10 | 110.7 | C5 | C10 | H11 | 117.2 |
| H10 | C10 | H11 | 102.3 | N5 | C11 | C12 | 121.5(4) |
| N5 | C11 | C16 | 116.3(4) | C12 | C11 | C16 | 122.2(4) |
| C11 | C12 | C13 | 117.9(4) | C11 | C12 | H13 | 122.5 |
| C13 | C12 | H13 | 119.6 | O1 | C13 | C12 | 123.4(4) |
| O1 | C13 | C14 | 115.5(4) | C12 | C13 | C14 | 121.1(4) |
| O2 | C14 | C13 | 120.3(4) | O2 | C14 | C15 | 120.3(4) |
| C13 | C14 | C15 | 119.4(4) | O3 | C15 | C14 | 114.3(4) |
| O3 | C15 | C16 | 123.9(5) | C14 | C15 | C16 | 121.7(4) |
| C11 | C16 | C15 | 117.7(4) | C11 | C16 | H23 | 119.2 |
| C15 | C16 | H23 | 122.7 | O1 | C17 | H14 | 108.6 |
| O1 | C17 | H15 | 114.6 | O1 | C17 | H16 | 103.3 |
| H14 | C17 | H15 | 117.2 | H14 | C17 | H16 | 105.5 |
| H15 | C17 | H16 | 106.2 | O2 | C18 | H17 | 108.9 |
| O2 | C18 | H18 | 109.5 | O2 | C18 | H19 | 102.6 |
| H17 | C18 | H18 | 110.7 | H17 | C18 | H19 | 106.9 |
| H18 | C18 | H19 | 117.7 | O3 | C19 | H20 | 101.8 |
| O3 | C19 | H21 | 111.0 | O3 | C19 | H22 | 115.0 |
| H20 | C19 | H21 | 114.1 | H20 | C19 | H22 | 113.9 |
| H21 | C19 | H22 | 101.6 | | | | |

TABLE 5

Least-Squares Planes in TMH

| Quinazoline Plane | | Trimethoxyanilino Plane | |
|---|---|---|---|
| Atom | Distance | Atom | Distance |
| N1 | −0.022(4) | C11 | −0.007(4) |
| N2 | 0.022(4) | C12 | −0.004(4) |
| C1 | −0.059(4) | C13 | 0.013(4) |
| C2 | 0.012(4) | C14 | −0.010(4) |
| C3 | 0.045(5) | C15 | 0.000(4) |
| C4 | 0.030(4) | C16 | 0.012(5) |
| C5 | −0.034(4) | | |
| C6 | −0.051(4) | | |
| C7 | −0.005(4) | | |
| C8 | 0.064(4) | | |

Statistical

| Plane | Mean Deviation | $\chi^2$ |
|---|---|---|
| Quinazoline | 0.0345 | 809.4 |
| Trimethylanilino | 0.0077 | 25.4 |
| Dihedral Angle Between Planes: | 107.52° | |

TABLE 6

Hydrogen Bonding Interactions in TMH

| A | H | B | A–H (Å) | H...B (Å) | A...B (Å) | A–H...B(°) |
|---|---|---|---|---|---|---|
| O4 | H24 | N2 | 0.92 | 2.04 | 2.913(5) | 159.4 |
| O4 | H25 | O2 | 0.87 | 2.13 | 2.923(4) | 151.0 |
| N3 | H2 | N1 | 0.94 | 2.01 | 2.943(5) | 171.3 |
| N5 | H12 | O4 | 1.09 | 1.96 | 3.021(5) | 166.0 |
| N3 | H2 | N2 | 0.94 | 3.13 | 2.300(4) | 114.1 |

6.2. EXAMPLE 2: ELEMENTAL ANALYSIS OF TMH

Two samples of trimetrexate monohydrate were analyzed for carbon, hydrogen and nitrogen content. The results for both samples are presented in Table 7. Trimetrexate monohydrate, $C_{19}H_{23}O_3N_5 \cdot H_2O$, has a molecular weight of 387.44 g/mol. The theoretical values presented in Table 7 are based on the elemental composition of the monohydrate. The data show good agreement with the expected results for the monohydrate.

TABLE 7

Elemental Analysis of C, H and N in TMH

| Element | Sample 1 (%) | Sample 2 (%) | Theoretical (%) |
|---|---|---|---|
| Carbon | 59.14 | 59.08 | 58.90 |
| Hydrogen | 6.55 | 6.63 | 6.50 |
| Nitrogen | 18.04 | 18.22 | 18.08 |

6.3. EXAMPLE 3: MASS SPECTROMETRY

Mass spectra were taken of two samples of trimetrexate monohydrate. The spectra were measured with a Hewlett-Packard 5989A MS Engine mass spectrometer with a hyperbolic quadrupole mass filter. The ionization method was direct electron impact, at an ionization energy of 70 eV. The probe was programmed from 45° C. to 250° C. at a rate of 25° C./min.

The mass spectra for the two samples were equivalent. Both the molecular ion and the base m/z=187 ion (M⁺ minus the trimethoxyanilino moiety) were clearly present. The major fragment ions observed, their relative intensities and assigned identities are presented in Table 8.

TABLE 8

Mass Spectrometry Data

| m/z | Relative Abundance (%) | Identity |
|---|---|---|
| 369 | 11 | M+ |
| 187 | 100 | M+- TMA |
| 183 | 14 | TMA.H+ |
| 170 | 17 | m/z 187 - NH3 |
| 168 | 16 | TMA.H+- CH3 |

TMA = the 3,4,5-trimethoxyanilino moiety of trimetetrexate

6.4. EXAMPLE 4: THERMOGRAVIMETRIC ANALYSIS

Two samples of trimetrexate monohydrate were analyzed using a DuPont 951 TGA module and a TA Instruments Thermal Analyst 2000 interface. The data were analyzed with the DuPont TGA v5.14A software. Each of the samples analyzed was between 5 and 6 mg in size. In order to ensure that the instrument would accurately analyze samples of that size, a control run was made with a sulfaguanidine standard (Sigma). Sulfaguanidine has a theoretical loss of volatiles of 7.5%. In the control run, a 6.0870 mg sample of sulfaguanidine was used. The sample was heated from 25° C. to 150° C. at a rate of 5° C./min, with a nitrogen gas flow rate of 50 cc/min. A loss of 7.837% volatiles was observed, corresponding to a positive error of about 4.5%.

Figure 4:
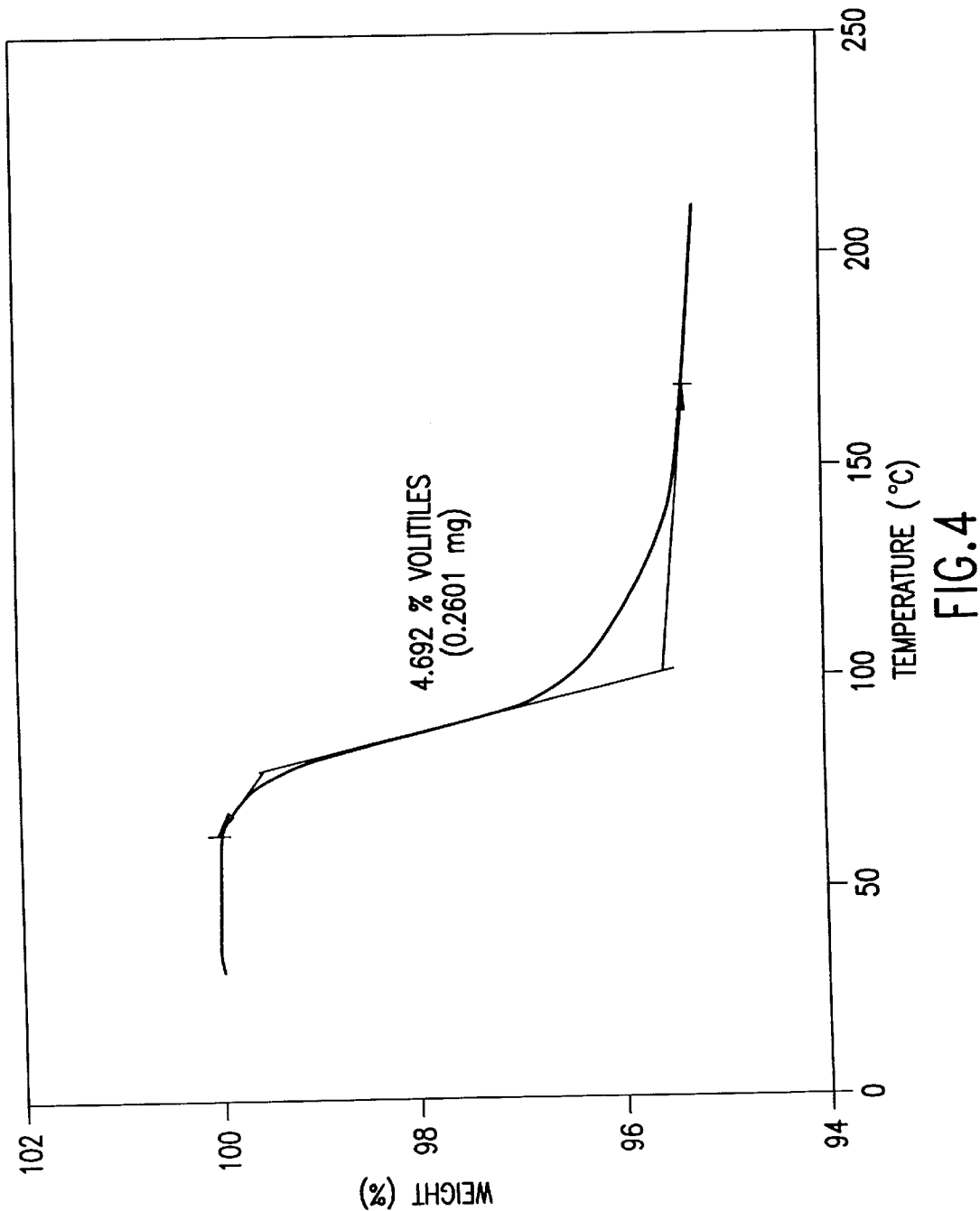
FIG. 4 shows the thermogravimetric analysis (TGA) result for a sample of TMH.

Two samples of TMH were subsequently analyzed, under the same experimental conditions as the sulfaguanidine control run, except that the temperature range was extended to about 210° C. A 5.5440 mg sample of TMH showed a volatile loss of 0.2601 mg, or 4.692%, and a 5.4350 mg sample showed a loss of 0.2578 mg, or 4.743%. The theoretical volatile loss for TMH is 4.65%. The TGA curve obtained for one of the two TMH samples (the 5.5440 mg sample) is shown in FIG. 4.

Two additional samples of TMH were analyzed using a DuPont 1090 Thermal Analyzer operating with the TGA Analysis V2.0 software. Accurately weighed samples of similar weight were heated from 25° C. to 200° C. at a rate of 10° C./min. The two samples showed losses of 4.57% and 4.56%.

6.5. EXAMPLE 5: DIFFERENTIAL SCANNING CALORIMETRY

Two samples of TMH were analyzed using a DuPont 1090 Thermal Analyzer operating with the Interactive DSC V3.0 software. Accurately weighed samples of similar weight were heated from 25° C. to 300° C. at a rate of 10° C./min.

Figure 5:
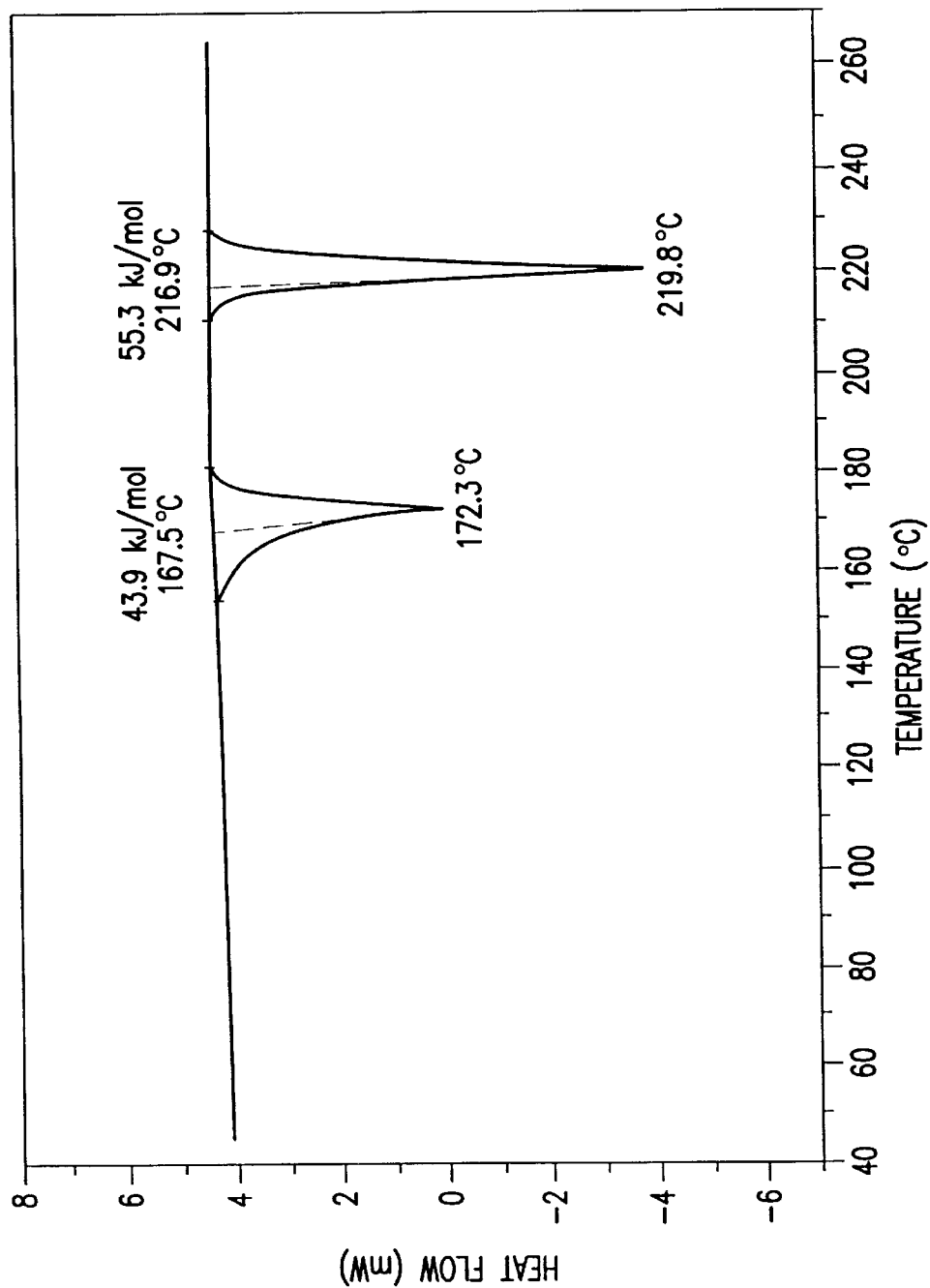
FIG. 5 shows the differential scanning calorimetry (DSC) result for a sample of TMH.

The DSC scan for one of the two samples is shown in FIG. 5. Two endotherms were observed for each sample, at similar temperatures, as shown below:

| Endotherm | Sample 1 | Sample 2 |
|---|---|---|
| First | 166.5–172.3° C. | 159.9–169.9° C. |
| Second | 216.4–219.8° C. | 217.5–220.7° C. |

The first endotherm is consistent with the loss of water from the crystal matrix, and the second endotherm is the melt. This conclusion was verified through visual observation of samples heated in a similar fashion with a Buchi melting point apparatus. At the 160–175° C. temperature range, no melting or "wetting" of the samples was observed. Sample 1 was observed to melt at 219.5 to 222.5° C., and Sample 2 was observed to melt at 218.5 to 221.5° C.

Figure 6:
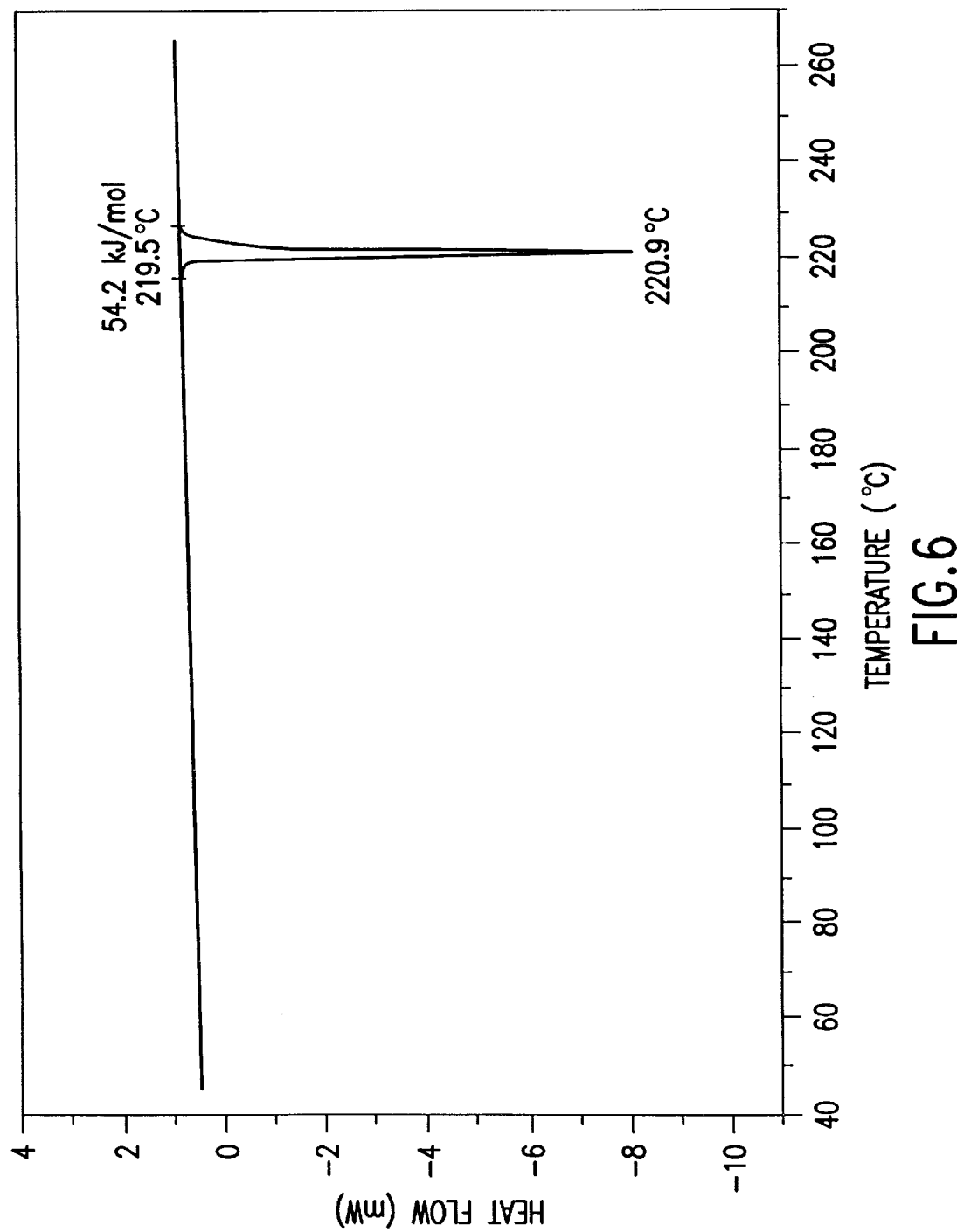
FIG. 6 shows a DSC scan of a sample of TMH which has been heated to 180° C. and then cooled to 25° C., prior to obtaining this DSC data.

The thermal behavior of trimetrexate monohydrate was investigated further using a different heating pattern. Two samples were heated past the first endotherm (to 180° C.), cooled, and then heated again from 25° C. to 230° C. In the second heating cycle, only an endotherm at about 220–221° C. was observed. This result is consistent with the loss of water during the first heating cycle. Once the water is lost from the crystal during the first heating cycle, it cannot reassociate with the trimetrexate molecules in the same fashion. Hence, the second heating cycle shows only a single endotherm, corresponding to the melt. The DSC trace is shown in FIG. 6.

6.6. EXAMPLE 6: THERMAL STABILITY OF TMH RELATIVE TO ANHYDROUS TRIMETREXATE

Samples of trimetrexate monohydrate and anhydrous trimetrexate were analyzed to compare the thermal stability of anhydrous trimetrexate with the trimetrexate monohydrate of the present invention.

Anhydrous Trimetrexate

Anhydrous trimetrexate was prepared by dehydrating trimetrexate monohydrate. A sample of trimetrexate monohydrate (about 30 g) was placed in a Petri dish and dried in a vacuum dessicator over phosphorus pentoxide. The sample was dried at a pressure of about 100 microns for 6 days.

Assay Procedure

The following procedure was used to assay the purity of trimetrexate monohydrate and anhydrous trimetrexate samples. Samples of the compounds were analyzed by HPLC.

The mobile phase is prepared by first dissolving 5 g of sodium dodecyl sulfate (Aldrich 86,201-0 or equivalent) in 1100 mL water and adjusting the pH to 3.0 with glacial acetic acid (about 5 mL). 825 mL of HPLC grade acetonitrile is then added, and the solution mixed thoroughly, while avoiding excessive foaming. The unfiltered solution is then degassed by sonicating for 5 minutes. The solution is degassed immediately before use, and at the beginning of each day.

Duplicate standard solutions are prepared with a trimetrexate reference compound at a concentration of 0.2 mg/mL in the mobile phase solution ("STD-1" and "STD-2"). The standard solutions are stored under refrigeration when not in use, and fresh solutions are prepared daily. Sample solutions of anhydrous trimetrexate and trimetrexate monohydrate are also prepared at 0.2 mg/mL in the mobile phase solution. The system is checked before testing the sample solutions by analyzing the reproducibility of trimetrexate peak area measurements for six injections of the standard trimetrexate solution (STD-1), trimetrexate peak symmetry, and agreement between the duplicate standard preparations. The acceptance criteria are as follows:

Reproducibility: <2.0% RSD

Symmetry: <2.0 (tailing factor)

Standard Agreement: <2%

Average trimetrexate peak areas are used to calculate corrected standard areas, as described below.

For assay data, the HPLC operating parameters are as follows:

| | |
|---|---|
| Flow Rate: | 1.5 mL/minute |
| Detection Wavelength: | 235 nm |
| Injection Volume: | 10 μL |
| Column Temperature: | ambient (15–30° C.) |
| Run Time: | 12 minutes (1 minute after the trimetrexate peak) |
| Typical Integration: | attenuation 32 for first 8 minutes, then 512 |

Each sample solution is run, and the purity is calculated.

For the determination of impurities, the operating parameters are as before, except that the run time is extended to 30 minutes to detect all possible impurities and/or degradation products, and an attenuation of 32 is used. A mobile phase blank is first run, followed by a sample solution.

The calculations are made as follows:

$C_{STD}$=(mg STD x purity STD (as a decimal))÷100 mL

Corr. Std. Area=Std. Peak Area÷$C_{STD}$

Avg. Corr. Std. Area=(Corr. Std. Area (STD-1)+Corr. Std. Area (STD-2))÷2 mg found =(Area Samp.÷Avg. Corr. Std. Area)×dilution mL

Purity (%w/w)=[(mg found×100%)÷mg sample weighed)] ×[100÷(100−M)] where M is the percent moisture.

For the impurity calculations, peaks not present in the blank chromatogram (and not from solvent front disturbances) are identified, and the following calculations performed:

Relative Retention Time (RRT)=$r_{imp}/r_{TMTX}$

Peak Area (%)=[peak area (imp)÷(speak area (all impurities+TMTX))] ×100.

Results

Samples of the anhydrous and monohydrate compounds were initially assayed for purity and moisture content. The samples were stored for 4 weeks at either 25° C. or 50° C. HPLC chromatograms were recorded for the samples stored at each temperature after 3 days, 1 week, 2 weeks and 4 weeks of storage, and the samples assayed at each time interval for purity, impurities and water content.

FIG. 7 shows the HPLC chromatograms for the samples stored at 50° C. for 4 weeks. In FIG. 7, trace A shows the chromatogram for the anhydrous sample, B shows trimetrexate monohydrate, and C is a solvent blank. The peak at about 13 minutes corresponds to the non-degraded compound; this peak is truncated in the Figure in order to expand the y-axis to view the impurities. FIG. 7 shows impurities in the anhydrous sample in the 2 to 7 minute region and a large impurity at about 20 minutes. In contrast to the anhydrous sample, trimetrexate monohydrate showed no significant degradation products after 4 weeks at 50° C. Table 9 summarizes the stability data.

TABLE 9

Thermal Stability of TMH

| Sample | Time | Assay (w/w) | Amine (% area) | Total Impurities (% area) | % Moisture |
|---|---|---|---|---|---|
| Monohydrate at 25° C. | Initial | 99.6 | 0.1 | 0.2 | 4.9 |
| | 3 days | 101.4 | 0.1 | 0.2 | 4.7 |
| | 1 week | 96.3 | 0.1 | 0.1 | 4.5 |
| | 2 weeks | 99.4 | 0.1 | 0.1 | 4.9 |
| | 4 weeks | 99.6 | 0.1 | 0.3 | 4.3 |
| at 50° C. | 3 days | 99.4 | 0.1 | 0.3 | 4.7 |
| | 1 week | 98.6 | 0.1 | 0.2 | 4.6 |

TABLE 9-continued

Thermal Stability of TMH

| Sample | Time | Assay (w/w) | Amine (% area) | Total Impurities (% area) | % Moisture |
|---|---|---|---|---|---|
| | 2 weeks | 98.7 | 0.1 | 0.1 | 4.8 |
| | 4 weeks | 99.6 | 0.2 | 0.3 | 4.4 |
| Anhydrous at 25° C. | Initial | 98.5 | 0.2 | 0.3 | 0.1 |
| | 3 days | 100.4 | 0.2 | 0.4 | 0.3 |
| | 1 week | 96.6 | 0.3 | 0.4 | 0.4 |
| | 2 weeks | 98.4 | 0.4 | 0.5 | 0.2 |
| | 4 weeks | 97.6 | 0.8 | 1.0 | <0.1 |
| at 50° C. | 3 days | 99.5 | 0.4 | 0.7 | 0.4 |
| | 1 week | 95.0 | 0.7 | 1.2 | 0.7 |
| | 2 weeks | 95.8 | 1.4 | 2.1 | 0.3 |
| | 4 weeks | 92.7 | 2.9 | 4.5 | <0.1 |

The "amine" entry in Table 9 corresponds to the amine degradation product which is prominent in FIG. 7 as the large peak at about 20 minutes in the anhydrdous sample. This degradation product was isolated and identified as 6-aminomethyl-5-methyl-2,4-quinazolinediamine. It is a pale yellow powder, with a molecular formula of $C_{10}H_{13}N_5$ and a formula weight of 203.25 g/mol. The structure of the compound is shown below

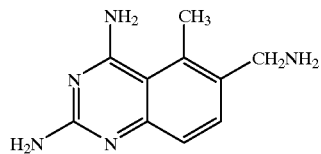

The ultraviolet absorption spectrum of the degradation product was measured using an IBM 9420 UV/VIS spectrophotometer. A 0.005 g/L solution of the compound in methanol was prepared, and the spectrum was measured using 1.0 cm cells. The molar absorptivities of the three principal absorption maxima are shown in Table 10.

TABLE 10

Absorption Maxima and Absorptivities of Anhydrous Trimetrexate Degradation product

| λ (nm) | Molar Absorptivity (ε) |
|---|---|
| 240 | 3.7208 × 10$^4$ |
| 274 | 8.371 × 10$^3$ |
| 343 | 3.720 × 10$^3$ |

6.7. EXAMPLE 7: PREPARATION OF TRIMETREXATE MONOHYDRATE FROM TRIMETREXATE ACETATE HYDRATE

Trimetrexate monohydrate was produced from trimetrexate acetate hydrate, according to the method of Scheme 1.

6.7.1. MATERIALS

The materials used and their source, or a representative source, are shown in Table 11. In each step of the synthesis, the reagent vessel (a steel reactor) is first cleaned, dried, and purged with nitrogen.

TABLE 11

Materials in TMH synthesis

| Chemical Name | Form Used | Supplier (or equivalent) |
|---|---|---|
| Raw Materials | | |
| trimetrexate acetate, crude | crystalline | Bioscience (Parke-Davis) |
| Reagents | | |
| ammonia | 25% sol. | Staub, Jäkle |
| gluconic acid | 35–55% sol. | Fluka |
| glacial acetic acid | liquid | Wacker |
| sodium chloride | crystalline | Jäkle |
| Reagents with Catalytic Amount Input | | |
| sodium metabisulfite | crystalline | Jäkle |
| Solvents | | |
| n-butanol | liquid | Biesterfeld |
| deionized water | liquid | |
| ethanol | liquid | Jäkle, Staub |
| dimethylformamide | liquid | Jäkle (Biesterfeld) |
| Auxiliary Agents | | |
| tonsil (= bentonite) | powder | Sud-Chemie |
| Hyflo Supercel | powder | Jäkle |
| activated charcoal | powder | Jäkle, Biesterfeld |
| Intermediate products | | |
| trimetrexate base, crude | crystalline | |
| trimetrexate base, DMF adduct, pure | crystalline | |
| trimetrexate hydrochloride | crystalline | |
| Final product | | |
| trimetrexate monohydrate | sieved/blended | |

6.7.2. STEP 1: TRIMETREXATE BASE, CRUDE

The reactor is charged with 41.5 L of n-butanol and 10.4 L of deionized water. 6.3 kg of crude trimetrexate acetate is then added. Then, 3 g of sodium metabisulfite, 0.65 L of ammonia, 1 kg of tonsil and 1 kg of Supercel are added.

The reaction mixture is heated to 90° C. to a gentle reflux, and stirred for 10 minutes.

Thereafter, a pressure filtration is performed with a preheated filter tube at about 1 bar, into PE-drums. The tube is rinsed afterwards with a mixture of 4 L of n-butanol and 1 L of deionized water.

The filtrate is transferred into the cleaned reactor (cleaned by rinsing with 5 liters of a 4:1 n-butanol/deionized water mixture) and heated to 70° C. 1.95 L of ammonia is then added. The base crystallizes after about 5 minutes. The reaction mixture is cooled to 20° C. and filtered using vacuum. The filter cake is washed with 5 L of deionized water and 5 L of ethanol (80%, using 4 parts by volume ethanol and one part by volume of water). The yield is about 5.6 kg of humid substance, or 4.4±0.5 kg of dried product (calculated), corresponding to a yield of 84±10% relative to crude trimetrexate acetate.

6.7.3. STEP 2: TRIMETREXATE BASE, DMF ADDUCT

The reaction vessel is charged with 10.4 L of dimethylformamide (DMF) and 1.04 L of deionized water, then 4.35 kg of the trimetrexate base (dried) of Step 1 is added. The solution is heated to 100° C., then cooled to 75° C., and 5.2 L of ethanol are added. The solution is further cooled to 55–60° C. and maintained until crystallization occurs. After crystallization, the solution is cooled to 10° C. and filtered using vacuum. The crystals are washed twice with 2.6 L of ethanol (80% v/v). Alternatively, the same procedure can be used starting with 4.7 kg (referred to dried substance) of the humid yield of trimetrexate base of step one.

The yield is 3.9±0.5 kg of humid product, or 3.0±0.3 kg of dried substance (calculated), corresponding to a yield of 69±7% relative to the crude trimetrexate base starting material.

6.7.4. STEP 3: TRIMETREXATE HYDROCHLORIDE 2.85 kg of the trimetrexate DMF adduct of step 2 (referred to dried material) is suspended in 45 L of warm deionized water and heated to 50° C. 3.9 kg of gluconic acid (35–55% aqueous solution; weight referred to content of 50%) is added, resulting in a dark, cloudy solution. 0.05 kg of activated charcoal and 0.1 kg of Supercel are added, and the mixture is stirred for 10 minutes at 50° C. The mixture is then pressure filtered at 0.5 bar into PE-drums and the filter pipeline is rinsed with 5 L of warm deionized water.

The reaction vessel is cleaned thoroughly with warm water, and the filtrate is recycled into the vessel. 0.167 L of glacial acetic acid at 50° C. is added, followed by a solution of 0.583 kg sodium chloride in 2.5 L deionized water. During this operation, the product is crystallizing. The suspension is stirred for 10 minutes at 45–50° C. and cooled thereafter to 20° C. It is then filtered and washed with 5 L of deionized water and 5 L of ethanol (80% v/v). The yield of humid substance is 4.0±0.5 kg, or 2.6±0.3 kg of dried substance, corresponding to a yield of 87±10% relative to the trimetrexate base DMF adduct starting material.

6.7.5. STEP 4: TRIMETREXATE MONOHYDRATE 2.86 kg of trimetrexate hydrochloride from Step 3 is suspended in 30 L of deionized water and 10 L of n-butanol. The mixture is heated to 80° C. and without further heating, 0.833 L of ammonia (25%) is added. The hydrochloride initially dissolves, but after about 2 minutes the base precipitates. The mixture is stirred at 70–80° C. for 10 minutes and cooled thereafter to 10° C., followed by filtration using a vacuum nutsche. The filtrate is washed with 5 L of deionized water and 5 L of ethanol (80% v/v). The humid material is dried under vacuum at 20–30 mbar for 15–20 hours at 60° C. in a vacuum tray dryer, or preferably at 50° C. for about 4-8 hours in a rotary vacuum dryer.

Immediately after drying, the product is sieved with a mesh of 0.5 mm at maximum rotor speed. The batch-wise unit container (fibre drum) with PE insert (folding bag) is directly connected to the exit funnel of the sieving machine by means of a tension belt. From the operation platform the dried product is given in portions into the feeding space of the sieving machine.

Immediately after sieving, the product is transferred to the blender, and the material is blended for 30 minutes.

The yield of humid substance is 2.9±0.5 kg, or 2.4±0.2 kg of sieved substance, corresponding to a yield of 92±8% relative to the trimetrexate hydrochloride starting material.

6.8. EXAMPLE 8: PREPARATION OF TRIMETREXATE MONOHYDRATE FROM A QUINAZOLINE ALDEHYDE FORMATE

Trimetrexate monohydrate can be produced from quinazoline aldehyde formate or diformate, according to the method of Scheme 2. The following is a process to produce a typical batch (3.5 kg) of trimetrexate monohydrate, using the diformate starting material.

6.8.1. MATERIALS

All materials are readily available from various commercial suppliers. The starting material, quinazoline aldehyde formate or diformate, can be synthesized by reduction of the corresponding nitrile, 2,4-diamino-5-methyl-6-quinazoline carbonitrile, with Raney nickel and formic acid (see *Biochem. Pharmacology*, 33, 3251 (1984)). In each step of the synthesis, the reagent vessel (a steel reactor) is first cleaned, dried, and purged with nitrogen.

6.8.2. STEP 1: QUINAZOLINE ALDEHYDE BASE

The reaction vessel (400 L enameled stainless steel reactor) is charged with a mixture of 13.5 L n-butanol and 9 L of water. To this is added 5.4 kg of quinazoline aldehyde diformate. After addition of 90 g of EDTA, the mixture is heated to 80° C. At this temperature, 0.9 L of TEA and 2.25 L of ammonia are added, raising the pH to >8.5. The mixture is heated to 90° C. (gentle reflux) and stirred at this temperature for 20 minutes.

Thereafter, the suspension is cooled to 20–25° C. and filtered by suction. Filtered portions are washed with at least 1.8 L of n-butanol, 1.8 L of ethanol and 1.8 L of water. A sample is taken for control testing according to appearance (olive brown to yellow powder, humid) and NMR spectrum.

A typical yield is 3.6 to 3.9 kg (dry basis), corresponding to 89 to 97% relative to the quinazoline aldehyde diformate starting material.

6.8.3. STEP 2: QUINAZOLINE SCHIFF BASE

The reaction vessel (400 L enameled steel reactor) is charged with 22 L of n-butanol and 4.4 L of toluene. 3.87 kg of wet quinazoline aldehyde base (from Step 1; referred to dry weight) and 3.38 kg of 3,4,5-trimethoxyaniline are added and the mixture is dehydrated by an azeotropic distillation from 89° C. up to 110° C. liquid phase temperature, yielding approximately 0.64 L of aqueous phase. The quantity of water generated is used as a control to monitor the progress of the reaction.

Thereafter, the mixture is cooled to 20–25° C. and the Schiff base is filtered off by suction. Filtered portions are washed with at least 3.5 L of n-butanol and 2.5 L of t-butyl methyl ether. A sample is taken for control testing according to appearance (yellowish to brownish little plates) and NMR spectrum, and the Schiff base is taken directly to the next step to minimize contact with moisture (humidity) due to the hydrolytic nature of the Schiff base. (See Section 5.4, above.)

A typical yield is 5.3 to 6.4 kg (dry basis), corresponding to 82 to 99% relative to the quinazoline aldehyde base starting material.

6.8.4. STEP 3: TRIMETREXATE ACETATE

The reaction vessel (400 L enameled steel reactor) is charged with 30 L of tetrahydrofuran (THF), 7.3 L of water, 270 g of sodium carbonate, 5.85 kg of quinazoline Schiff base (from step 2; referred to dry weight) and 165 g of 3,4,5-trimethoxyaniline. The mixture is heated to approximately 45° C. A solution of 0.55 kg of sodium borohydride dissolved in 2.7 L of water and 5 mL of sodium hydroxide is slowly added over 3–5 hours to the reactor, during which time the reactor is flushed with nitrogen. After completion of the addition of sodium borohydride solution, the reaction is stirred for 10 minutes at 63–65° C. The progress of the reaction is monitored by TLC. If the amount of starting material is >0.5%, an additional amount of sodium borohydride (calculated on a molar basis) is added to the refluxing reaction.

Approximately 27 L of THF is distilled off under normal pressure at 65–68° C. 10 L of n-butanol and 5 L of water are added. Approximately 5 L of a THF/butanol/water mixture is distilled off until the temperature of the reaction mixture reaches 85° C. The reaction is then cooled to 5–10° C. and the two-phase mixture is filtered by vacuum. Each filtered portion is washed with at least 10 L of water.

The crude damp trimetrexate base (5.65 kg) is suspended in a mixture of 32 L of ethanol and 9 L of water. This suspension is heated to 70° C. and 0.76 L of lactic acid and 0.685 L of acetic acid are added. The resulting solution is mixed with 0.35 kg of Tonsil and 0.1 kg of activated charcoal and the solution is pressure filtered at 0.5 bar at 70° C.

To the filtrate is added 0.59 kg of sodium acetate in 2.3 L of water and 1 L of glacial acetic acid. The mixture is stirred for 30 minutes at 70–75° C. After cooling to 20° C., the suspension obtained is vacuum filtered. Each filtered portion is washed with at least 4.5 L of acetic acid. A sample is taken for control testing according to appearance (yellow-green solid, humid), HPLC retention time, and HPLC assay (NLT 98% w/w on an anhydrous basis).

A typical yield is 5.5 to 6.5 kg (dry basis), corresponding to 77 to 91% relative to the quinazoline Schiff base starting material.

6.8.5. STEP 4: TRIMETREXATE MONOHYDRATE

The reaction vessel (400 L enameled steel reactor) is charged with 47 L of n-butanol and 8 L of water. 6 kg of trimetrexate acetate (from Step 3; referred to dry weight), 140 g of ascorbic acid, and 0.54 L of ammonia are added. The mixture is heated to 90° C. and stirred for 30 minutes until all of the material has dissolved. To the reaction mixture is added 0.3 kg of Tonsil and the reaction stirred for 10 minutes at 90° C. before being pressure filtered at 80° C. at 0.5 bar.

The filtrate is mixed with 0.67 L of sodium hydroxide and 1.48 L of ammonia at about 80° C. The mixture is cooled to 15–20° C. and stirred at this temperature for 30 minutes. The suspension obtained is vacuum filtered. Each filtered portion is washed with at least 4 L of water and 2.7 L of 2-propanol.

The reaction vessel is flushed with nitrogen and the trace amounts of 2-propanol in the product are removed using the following procedure. 2-methoxypropanol (31 L) and the wet trimetrexate base are fed into the reactor. The mixture is heated to 110–115° C. to remove traces of 2-propanol, and then allowed to cool to 105° C. Tonsil (0.5 kg) is added to the mixture. The reaction is again heated to 110–115° C. and pressure filtered at 0.5 bar and 110° C. The filtrate is cooled to 15–20° C. to effect crystallization. After 20 minutes stirring at 20° C, the product is filtered off by vacuum. Each filtered portion is washed with at least 4 L of 2-propanol.

Conversion of the 2-methoxypropanol adduct to the free base is performed as follows. The reactor is charged with 27 L of ethanol, 4.9 L of water and the 2-methoxypropanol adduct. The mixture is then heated to 78–80° C. at reflux, and stirred at this temperature for 30 minutes. After cooling to 15–20° C. to effect crystallization, the product is vacuum filtered. Each filtered portion is washed with at least 4 L of water.

The wet product is dried at 70° C. and 20–30 mbar for 15–20 hours in a vacuum tray dryer, or preferably at 50° C. and 20–30 mbar for about 4–8 hours in a rotary vacuum dryer. The dried trimetrexate monohydrate base is sieved (500µ) and blended. A representative sample is removed for release testing.

A typical yield is 4.1 to 5.0 kg (dry basis), corresponding to 79 to 96% relative to the trimetrexate acetate starting material.

If any of the steps of the synthesis fails to produce material which meets the control test specification, the material may undergo an additional recrystallization according to the same procedures described herein for each step. If the water or solvent content in Step 4 is out of specification, the drying, sieving and blending parts may be repeated.

6.9. EXAMPLE 9: CHARACTERIZATION OF QUINAZOLINE SCHIFF BASE

The structure and identity of the quinazoline Schiff base, 2,4-diamino-5-methyl-6-[(3,4,5-trimethoxyphenylimino)-methinyl]-quinazoline, were confirmed using a variety of analytical methods.

Ultraviolet Absorption

The ultraviolet absorption spectrum of the quinazoline Schiff base was measured using a Perkin-Elmer Lambda 2 UV spectrophotometer. A 0.005 g/L solution of quinazoline Schiff base was prepared in methanol, and the spectrum was obtained using 1.0 cm cells. The molar absorptivities of the compound at the three principal absorption maxima observed are shown in Table 12.

TABLE 12

Absorption Maxima and Absorptivities of Quinazoline Schiff Base

| λ (nm) | Molar Absorptivity (ε) |
|---|---|
| 205 | $3.9497 \times 10^5$ |
| 247 | $2.9929 \times 10^5$ |
| 352 | $2.7137 \times 10^5$ |

Infrared Absorption

The infrared spectrum was recorded using a Nicolet Model 740 infrared spectrophotometer. A potassium bromide pellet was prepared at a concentration of approximately 0.5% (w/w). The principal spectral features and their assignments are shown in Table 13.

TABLE 13

Infrared Spectrum of Quinazoline Schiff Base

| Wavenumber ($cm^{-1}$) | Assignment |
|---|---|
| 3550–3300 | —$NH_2$ stretch |
| 3146, 3114 | aromatic CH stretch |
| 2996–2800 | $CH_3$ stretch |
| 1662 | —C=N stretch |
| 1617 | —$NH_2$ deformation |
| 1607–1400 | aromatic C=C, C=N stretch |
| 1228 | =C—O stretch of aryl ether |
| 1128 | aromatic CH in-plane def. |
| 897 | aromatic CH out-of-plane def. |

Proton and $^{13}C$ NMR

The proton ($^1H$) NMR spectrum for the compound was measured at 300.136 MHz using a Bruker AMX300 NMR spectrometer. A spectral width of 4504.5 Hz was measured, using 32K data points with signal averaging of 16 scans. The sample was prepared by dissolving 37 mg in 1.0 mL of dimethylsulfoxide-$d_6$, to which had been added TMS as a reference. The spectral data are shown in Table 14.

TABLE 14

Proton NMR Spectrum of Quinazoline Schiff Base

| δ (ppm) | Multiplicity | # Protons |
|---|---|---|
| 8.88 | s | 1 |
| 8.14 | d, J=8.9 Hz | 1 |
| 7.10 | d, J=8.9 Hz | 1 |
| 6.96 | bs | 2 |
| 6.60 | s | 2 |
| 6.25 | bs | 2 |
| 3.83 | s | 6 |
| 3.67 | s | 3 |
| 2.92 | s | 3 |

A Difference NOE experiment was run to determine the configuration about the imine double bond and verify the chemical shift assignment of the proton on C7 of the quinazoline ring. With this experiment, a selected resonance is irradiated during the pulse delay. Protons that are within 5 to 7 angstroms of the irradiated proton experience an enhancement in their signal. Those protons experiencing an enhanced signal are identified by subtracting a normal spectrum from the enhanced one.

The imine proton was irradiated for the Difference NOE experiment and a strong enhancement was observed in the 2', 6' protons on the trimethoxyaniline ring and the 5-methyl protons of the quinazoline moiety. This enhancement shows that the expected trans configuration exists about the imine double bond, since a cis configuration could not yield an NOE enhancement to the 2', 6' protons. A weaker enhancement was observed in the resonance at 8.14 ppm, which identifies it as proton 7 on the quinazoline ring.

A $^{13}C$ NMR spectrum was also recorded, and was consistent with the quinazoline Schiff base structure.

Mass Spectroscopy

The mass spectrum of the compound was obtained using direct inlet electron impact ionization. The spectrum was measured with a HP 5989A MS Engine mass spectrometer with a hyperbolic quadrupole mass filter. The probe was programmed from 35° C. to 250° C. at 25° C./min. The ionization energy was 70 mass spectrum is presented in Table 15.

TABLE 15

Mass Spectrometry Data

| m/z | Relative Abundance (%) | Identity |
|---|---|---|
| 367 | 100 | $M^+$ |
| 350 | 84 | $M^+$ - $NH_3$ |
| 335 | 34 | $M^+$ - $CH_3OH$ |
| 200 | 32 | $M^+$ - trimethoxyphenyl |
| 185 | 70 | $M^+$ - TMA |
| 168 | 30 | [trimethoxybenzene]$^+$ |

TMA = the 3,4,5-trimethoxyanilino moiety of trimetrexate

Water Content

The water in the sample was measured by Karl Fisher titration. The sample was found to contain 1.0% water (0.21 mol).

Melting Point

The melting range was measured by differential scanning calorimetry, using a Shimadzu DSC-50 instrument. The melting range was found to be 245.4–247.5° C.

Elemental Analysis

The compound was analyzed for C, H and N content using a CEC Model 240-XA CHN Analyzer. The results are shown in Table 16.

TABLE 16

Elemental Analysis of C, H and N

| Element | Theoretical (%) | Measured (%) |
|---|---|---|
| Carbon | 61.51 | 61.81 |
| Hydrogen | 5.81 | 6.03 |
| Nitrogen | 18.86 | 19.39 |

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

All references cited in the present application are incorporated by reference in their entirety.

What is claimed is:

1. A thermally stable non-salt 2,4-diamino-5-methyl-6-[(3,4,5-trimethoxyanilino)methyl] quinazoline.

2. A thermally stable non-salt 2,4-diamino-5-methyl-6-[(3,4,5-trimethoxyanilino)methyl] quinazoline solvate.

3. The thermally stable non-salt of claim 2 wherein said solvate is a hydrate.

4. The thermally stable non-salt of claim 3 wherein said hydrate is a monohydrate.

5. The thermally stable non-salt of claim 2 wherein said thermally stable non-salt is crystalline.

6. The thermally stable non-salt of claim 2 wherein said thermally stable non-salt is substantially pure.

7. The thermally stable non-salt of claim 2 wherein said thermally stable non-salt is sterile.

8. A thermally stable crystalline non-salt hydrate of 2,4-diamino-5-methyl-6-[(3,4,5-trimethoxyanilino)methyl] quinazoline.

9. The thermally stable crystalline non-salt hydrate of claim 8 wherein said hydrate is a monohydrate.

10. 2,4-diamino-5-methyl-6-[(3,4,5-trimethoxyanilino)methyl] quinazoline monohydrate.

11. Crystalline 2,4-diamino-5-methyl-6-[(3,4,5-trimethoxyanilino)methyl] quinazoline monohydrate.

12. The crystalline 2,4-diamino-5-methyl-6-[(3,4,5-trimethoxyanilino)methyl] quinazoline monohydrate according to claim 11 having an X-ray powder diffraction pattern essentially the same as FIG. 1.

13. The crystalline 2,4-diamino-5-methyl-6-[(3,4,5-trimethoxyanilino)methyl] quinazoline monohydrate according to claim 11 having atomic coordinates as determined from an X-ray powder diffraction pattern, wherein said atomic coordinates are essentially the same as those provided by Table 2.

14. The crystalline 2,4-diamino-5-methyl-6-[(3,4,5-trimethoxyanilino)methyl] quinazoline monohydrate according to claim 11 wherein said compound is substantially pure.

15. Crystalline 2,4-diamino-5-methyl-6-[(3,4,5-trimethoxyanilino)methyl] quinazoline monohydrate belonging to the space group PT(#2) and having a triclinic cell with dimensions of a=7.699 Å, b=9.606 Å and c=13.012 Å.

16. The crystalline 2,4-diamino-5-methyl-6-[(3,4,5-trimethoxyanilino)methyl] quinazoline monohydrate according to claim 15 wherein said compound is substantially pure.

17. A pharmaceutical composition comprising a thermally stable non-salt 2,4-diamino-5-methyl-6-[(3,4,5-trimethoxyanilino)methyl] quinazoline and a pharmaceutically acceptable carrier.

18. A pharmaceutical composition comprising crystalline 2,4-diamino-5-methyl-6-[(3,4,5-trimethoxyanilino)methyl] quinazoline monohydrate and a pharmaceutically acceptable carrier.

19. The pharmaceutical composition of claim 17 or 18 wherein said thermally stable non-salt is crystalline.

* * * * *